US008882768B2

(12) United States Patent
Greep et al.

(10) Patent No.: US 8,882,768 B2
(45) Date of Patent: *Nov. 11, 2014

(54) HAND PIECE WITH ADJUSTABLE UTILITY CONDUIT

(71) Applicant: Megadyne Medical Products, Inc., Draper, UT (US)

(72) Inventors: Darcy W. Greep, Herriman, UT (US); Paul R. Borgmeier, Salt Lake City, UT (US); Chad S. Frampton, American Fork, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/831,379

(22) Filed: Mar. 14, 2013

(65) Prior Publication Data

US 2013/0204246 A1 Aug. 8, 2013

Related U.S. Application Data

(63) Continuation-in-part of application No. 13/541,210, filed on Jul. 3, 2012, which is a continuation-in-part of application No. 12/429,867, filed on Apr. 24, 2009, now Pat. No. 8,211,103.

(51) Int. Cl.
*A61B 18/18* (2006.01)
*A61B 17/00* (2006.01)
*A61B 18/14* (2006.01)
*A61B 18/00* (2006.01)

(52) U.S. Cl.
CPC .............. *A61B 18/14* (2013.01); *A61B 18/1402* (2013.01); *A61B 2218/006* (2013.01); *A61B 2018/00607* (2013.01); *A61B 18/1477* (2013.01); *A61B 2217/005* (2013.01); *A61B 2218/008* (2013.01); *A61B 17/00* (2013.01); *A61B 2018/00595* (2013.01); *A61B 2018/00601* (2013.01)
USPC .......................................................... 606/42

(58) Field of Classification Search
CPC ................. A61B 2218/008; A61B 2018/0091; A61B 2018/00916; A61B 2018/00595; A61B 2018/00601; A61B 2017/0042; A61B 2017/00424; A61B 2017/00455; A61C 1/10; A61C 1/12; A61C 1/141; A61C 1/147; A61C 17/225; A61C 17/34; A61C 19/004; B25F 1/02; B25F 1/04; B25F 5/02; B23B 45/00; B25G 11/102; F19P 3/18
USPC ...................................................... 606/41, 42
See application file for complete search history.

(56) References Cited

U.S. PATENT DOCUMENTS 2,311,424 A   2/1943   Weller, Jr.
2,329,439 A   9/1943   Hanssen (Continued)

FOREIGN PATENT DOCUMENTS

BZ   2107230   10/1992
CA   2111617   7/1994

(Continued)

OTHER PUBLICATIONS

U.S. Appl. No. 12/429,867, Feb. 3, 2012, Office Action.

(Continued)

*Primary Examiner* — Andrew Gilbert
(74) *Attorney, Agent, or Firm* — Workman Nydegger

(57) ABSTRACT

An electrosurgical instrument that reduces the amount of fatigue experienced by a physician performing electrosurgery includes a hand piece with a utility conduit connected to the hand piece at a central portion of the hand piece. The utility conduit can include an electrical cable and a smoke/fluid evacuation hose. The hand piece can include a channel system that receives a portion of the utility conduit therein and allows a physician to adjust the location on the hand piece at which the utility conduit exits the hand piece. Adjusting the location on the hand piece at which the utility conduit exits the hand piece can reduce the resistance to the movement of the electrosurgical instrument created by the weight of the utility conduit, which leads to less fatigue in a physician's hand during electrosurgery.

16 Claims, 10 Drawing Sheets

(56) References Cited

U.S. PATENT DOCUMENTS

| | | |
|---|---|---|
| 2,426,214 A | 8/1947 | Hewes |
| 2,530,962 A | 11/1950 | Hare |
| 2,542,019 A | 2/1951 | Fischer |
| 4,112,950 A | 9/1978 | Pike |
| 4,203,444 A | 5/1980 | Bonnell et al. |
| 4,545,375 A | 10/1985 | Cline |
| 4,562,838 A * | 1/1986 | Walker ............................ 606/42 |
| 4,688,569 A | 8/1987 | Rabinowitz |
| 4,911,159 A | 3/1990 | Johnson et al. |
| 4,921,492 A | 5/1990 | Schultz et al. |
| 4,936,842 A | 6/1990 | Amelio et al. |
| 5,055,100 A | 10/1991 | Olsen |
| 5,066,294 A | 11/1991 | Cosmescu |
| 5,085,657 A | 2/1992 | Ben-Simhon |
| 5,088,997 A | 2/1992 | Delahuerga et al. |
| 5,108,389 A | 4/1992 | Cosmescu |
| 5,114,422 A | 5/1992 | Cosmescu |
| 5,160,334 A | 11/1992 | Billings et al. |
| 5,195,959 A | 3/1993 | Smith |
| 5,196,007 A | 3/1993 | Ellman et al. |
| 5,199,944 A | 4/1993 | Cosmescu |
| 5,217,457 A | 6/1993 | Delahuerga et al. |
| 5,226,904 A | 7/1993 | Gentelia et al. |
| 5,234,428 A | 8/1993 | Kaufman |
| 5,244,462 A | 9/1993 | Delahuerga et al. |
| 5,302,354 A | 4/1994 | Watvedt et al. |
| 5,304,763 A | 4/1994 | Ellman et al. |
| 5,312,397 A | 5/1994 | Cosmescu |
| 5,318,516 A | 6/1994 | Cosmescu |
| 5,358,552 A | 10/1994 | Seibert et al. |
| 5,364,395 A | 11/1994 | West |
| 5,376,089 A | 12/1994 | Smith |
| 5,395,312 A | 3/1995 | Desai |
| 5,413,575 A | 5/1995 | Haenggi |
| 5,423,779 A | 6/1995 | Yeh |
| 5,431,650 A | 7/1995 | Cosmescu |
| 5,458,586 A | 10/1995 | Adiletta |
| 5,514,089 A | 5/1996 | Walbrink et al. |
| 5,520,651 A | 5/1996 | Sutcu et al. |
| D372,086 S | 7/1996 | Grasso et al. |
| D373,190 S * | 8/1996 | Monson ........................ D24/112 |
| 5,575,789 A | 11/1996 | Bell et al. |
| 5,609,573 A | 3/1997 | Sandock |
| 5,613,966 A | 3/1997 | Makower et al. |
| 5,626,568 A | 5/1997 | Yeh et al. |
| 5,658,249 A | 8/1997 | Beland et al. |
| 5,674,219 A * | 10/1997 | Monson et al. ................. 606/45 |
| 5,685,838 A | 11/1997 | Peters et al. |
| 5,693,044 A | 12/1997 | Cosmescu |
| 5,797,901 A | 8/1998 | Cosmescu |
| 5,800,431 A | 9/1998 | Brown |
| 5,836,909 A | 11/1998 | Cosmescu |
| 5,836,944 A | 11/1998 | Cosmescu |
| 5,868,722 A | 2/1999 | Yeh et al. |
| 5,874,052 A | 2/1999 | Holland |
| 5,928,137 A | 7/1999 | Green |
| 5,951,548 A | 9/1999 | DeSisto et al. |
| 6,001,077 A | 12/1999 | Ellman et al. |
| 6,045,596 A | 4/2000 | Holland, Jr. et al. |
| 6,053,886 A | 4/2000 | Holland, Jr. et al. |
| D426,883 S | 6/2000 | Berman et al. |
| 6,099,525 A | 8/2000 | Cosmescu |
| 6,110,259 A | 8/2000 | Schultz et al. |
| 6,117,134 A | 9/2000 | Cunningham et al. |
| 6,142,995 A | 11/2000 | Cosmescu |
| 6,146,353 A | 11/2000 | Platt |
| 6,149,648 A | 11/2000 | Cosmescu |
| 6,258,088 B1 | 7/2001 | Tzonev et al. |
| 6,302,881 B1 | 10/2001 | Farin |
| 6,306,135 B1 | 10/2001 | Ellman et al. |
| 6,355,034 B2 | 3/2002 | Cosmescu |
| 6,368,309 B1 | 4/2002 | Yeh |
| 6,458,125 B1 | 10/2002 | Cosmescu |
| 6,524,307 B1 | 2/2003 | Palmerton et al. |
| 6,544,210 B1 | 4/2003 | Trudel et al. |
| 6,558,379 B1 | 5/2003 | Batchelor et al. |
| 6,576,033 B1 | 6/2003 | Booth |
| 6,585,791 B1 | 7/2003 | Garito et al. |
| 6,589,316 B1 | 7/2003 | Schultz et al. |
| 6,602,249 B1 | 8/2003 | Stoddard et al. |
| 6,616,658 B2 * | 9/2003 | Ineson ............................. 606/42 |
| 6,635,034 B1 | 10/2003 | Cosmescu |
| 6,663,610 B1 | 12/2003 | Thompson et al. |
| 6,685,665 B2 | 2/2004 | Booth et al. |
| 6,689,146 B1 | 2/2004 | Himes |
| 6,702,812 B2 | 3/2004 | Cosmescu |
| 6,746,504 B2 | 6/2004 | Booth |
| 6,749,608 B2 | 6/2004 | Garito et al. |
| D493,530 S * | 7/2004 | Reschke ...................... D24/144 |
| 6,881,236 B2 | 4/2005 | Schultz et al. |
| 6,896,672 B1 | 5/2005 | Eggers et al. |
| 6,942,650 B1 | 9/2005 | Schultz et al. |
| 6,974,458 B2 | 12/2005 | Muller et al. |
| 7,033,353 B2 | 4/2006 | Stoddard et al. |
| D521,641 S | 5/2006 | Reschke et al. |
| 7,083,601 B1 | 8/2006 | Cosmescu |
| 7,112,199 B2 | 9/2006 | Cosmescu |
| 7,141,049 B2 | 11/2006 | Stern et al. |
| 7,156,842 B2 | 1/2007 | Sartor et al. |
| 7,156,844 B2 | 1/2007 | Reschke et al. |
| 7,207,977 B2 | 4/2007 | Thompson et al. |
| 7,241,294 B2 | 7/2007 | Reschke |
| 7,244,257 B2 | 7/2007 | Podhajsky et al. |
| 7,258,712 B2 | 8/2007 | Schultz et al. |
| D555,803 S | 11/2007 | Garito et al. |
| 7,294,116 B1 | 11/2007 | Ellman et al. |
| 7,393,354 B2 | 7/2008 | Buchman, II et al. |
| 7,597,731 B2 | 10/2009 | Palmerton et al. |
| 7,717,890 B2 | 5/2010 | Drogue et al. |
| D616,986 S | 6/2010 | Biegen et al. |
| 7,761,188 B2 | 7/2010 | Palmerton et al. |
| 7,789,946 B2 | 9/2010 | Schultz et al. |
| 7,892,337 B2 | 2/2011 | Palmerton et al. |
| 7,935,109 B2 | 5/2011 | Cosmescu |
| 7,959,698 B2 | 6/2011 | Schultz et al. |
| 8,057,470 B2 * | 11/2011 | Lee et al. ........................ 606/41 |
| 8,095,241 B2 | 1/2012 | Palmerton et al. |
| 8,147,577 B2 | 4/2012 | Palmerton et al. |
| 8,211,103 B2 * | 7/2012 | Greep ............................. 606/42 |
| 8,235,982 B2 | 8/2012 | Ward |
| 8,414,576 B2 * | 4/2013 | Cosmescu ....................... 606/41 |
| D709,196 S * | 7/2014 | Greep et al. ................. D24/144 |
| 2006/0264928 A1 * | 11/2006 | Kornerup et al. ............... 606/45 |
| 2007/0129722 A1 | 6/2007 | Cosmescu |
| 2007/0249990 A1 | 10/2007 | Cosmescu |
| 2009/0018539 A1 * | 1/2009 | Cosmescu ....................... 606/41 |
| 2009/0125023 A1 * | 5/2009 | Stephen et al. ................. 606/42 |
| 2010/0094200 A1 | 4/2010 | Dean et al. |
| 2010/0094283 A1 | 4/2010 | Cosmescu |
| 2011/0190768 A1 | 8/2011 | Shvetsov et al. |
| 2012/0180664 A1 | 7/2012 | Lundquist |
| 2012/0197250 A1 | 8/2012 | Ward |
| 2012/0283718 A1 | 11/2012 | Cosmescu |
| 2012/0283728 A1 | 11/2012 | Cosmescu |
| 2012/0286179 A1 | 11/2012 | Palmerton et al. |
| 2013/0006236 A1 * | 1/2013 | Greep et al. .................... 606/34 |
| 2013/0204246 A1 * | 8/2013 | Greep et al. .................... 606/41 |

FOREIGN PATENT DOCUMENTS

| | | |
|---|---|---|
| CA | 2241516 | 7/1997 |
| CA | 2200535 | 9/1997 |
| CA | 2311424 | 7/1999 |
| CA | 2311434 | 7/1999 |
| CA | 2542019 | 7/1999 |
| CA | 2329439 | 10/1999 |
| CA | 2351649 | 5/2000 |
| CA | 2707676 | 5/2000 |
| CA | 2352880 | 8/2000 |
| CA | 2426214 | 5/2002 |
| CA | 2462825 | 4/2003 |
| CA | 2530962 | 1/2005 |
| CA | 2123960 | 7/2005 |
| CA | 2557280 | 10/2005 |

(56) References Cited

FOREIGN PATENT DOCUMENTS

| | | |
|---|---|---|
| CA | 2541694 | 10/2006 |
| CA | 2613950 | 11/2007 |
| CA | 2604402 | 3/2008 |
| CA | 2639108 | 2/2009 |
| CA | 2009151831 | 5/2009 |
| EM | 1584342 | 10/2005 |
| EP | 0447121 | 9/1991 |
| EP | 0538641 | 4/1993 |
| EP | 0729730 | 9/1996 |
| EP | 1016383 | 7/2000 |
| EP | 1188415 | 3/2002 |
| EP | 1388324 | 2/2004 |
| EP | 1532928 | 5/2005 |
| EP | 1707146 | 10/2006 |
| EP | 1795139 | 6/2007 |
| EP | 1902682 | 3/2008 |
| EP | 1938767 | 7/2008 |
| EP | 2438876 | 4/2012 |
| ES | 2159778 | 10/1998 |
| ES | 2238776 | 9/2005 |
| GB | 2452392 | 3/2009 |
| IL | 136254 | 3/1998 |
| IL | 139085 | 11/2001 |
| IL | 125102 | 7/2003 |
| IL | 159929 | 6/2004 |
| WO | 9108797 | 6/1991 |
| WO | 9219168 | 11/1992 |
| WO | 9623448 | 1/1996 |
| WO | 9619151 | 6/1996 |
| WO | 9723167 | 7/1997 |
| WO | 9931954 | 7/1999 |
| WO | 9953833 | 10/1999 |
| WO | 0028908 | 5/2000 |
| WO | 0032296 | 6/2000 |
| WO | 0238033 | 5/2002 |
| WO | 02060314 | 8/2002 |
| WO | 03030714 | 4/2003 |
| WO | WO2004006787 | 1/2004 |
| WO | 2005007214 | 1/2005 |
| WO | 2005094710 | 1/2005 |
| WO | 2005028078 | 3/2005 |
| WO | 2005046498 | 5/2005 |
| WO | 2007005159 | 1/2007 |
| WO | 2007123565 | 11/2007 |
| WO | 2008109014 | 9/2008 |
| WO | 2012/154699 | 5/2012 |

OTHER PUBLICATIONS

U.S. Appl. No. 12/429,867, Mar. 6, 2012, Notice of Allowance.
Medtronic PlasmaBlade Family website printout, printed from www.peaksurgical.com/products/plasmablade, on Jul. 2, 2012, 3 pages.

\* cited by examiner

HAND PIECE WITH ADJUSTABLE UTILITY CONDUIT

CROSS-REFERENCE TO RELATED APPLICATIONS

This application is a continuation in part of U.S. patent application Ser. No. 13/541,210, filed Jul. 3, 2012, entitled ELECTROSURGICAL INSTRUMENT WITH ADJUSTABLE UTILITY CONDUIT, which is a continuation in part of U.S. patent application Ser. No. 12/429,867, now U.S. Pat. No. 8,211,103, filed Apr. 24, 2009, entitled "ELECTROSURGICAL INSTRUMENT WITH ADJUSTABLE POWER CABLE," the disclosures of which are incorporated herein by this reference in their entireties.

BACKGROUND

1. Technical Field

This invention relates to hand-held instruments. More particularly, the invention relates to hand-held instruments that facilitate the performance of various procedures while reducing the amount of fatigue experienced by users performing the procedures.

2. The Relevant Technology

As is known to those skilled in the art, modern surgical techniques typically employ radio frequency (RF) power to cut tissue and coagulate bleeding encountered in performing surgical procedures. For a historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. A monopolar electrosurgical generator system has an active electrode, such as in the form of an electro surgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

To make the electrical connection for the RF current between the electrosurgical generator and the electrosurgical instrument, a cable having an electrically conductive core extends from the electrosurgical generator to the electrosurgical instrument. The cable may also include a cord with additional conductors. The cord provides a connection for transmitting control signals from the electrosurgical instrument to the electrosurgical generator. The control signals may be used to cause the generator to deliver RF currents to the electrosurgical instrument for different cutting modes such as cut, coagulate, and cut-coagulate blend.

When an electrosurgical instrument is used for cutting or coagulation, smoke is commonly produced. A surgeon or assistant uses a separate smoke evacuation device to remove the smoke from the surgical field. Smoke evacuation devices commonly include a suction wand connected to a vacuum device via tubing. The surgeon or assistant holds the suction wand close to the surgical site and the smoke is drawn into the suction wand and through the tubing. However, using a smoke evacuation device separate from the electrosurgical instrument is not ideal. Using a separate smoke evacuation device requires additional hands and instruments near the surgical site, which can obscure the surgeon's view of the surgical site and reduce the room available around the surgical site for the surgeon to move.

As a result, electrosurgical instrument and smoke evacuation combination devices have been developed. These combination devices often include a hand piece that can receive an electrode or tip for performing electrosurgical procedures. The hand piece is connected to a generator via a power cable to convey RF current to the electrode or tip. Additionally, a smoke evacuation hose is connected between the hand piece and a vacuum to draw smoke away from the surgical site. In some cases, the power cable runs through a portion of the smoke evacuation hose.

The power cables and smoke evacuation hoses have certain flexibility and weight characteristics that limit the ability of the physician during a surgical procedure. For example, the weight/moment-arm effect and drag of the power cable and/or the smoke evacuation hose as well as the connection location(s) of the power cable and/or smoke evacuation hose to the electrosurgical instrument limit the physician's ability to continually hold and use the electrosurgical instrument. The electrode or tip is received within one end of the hand piece (commonly referred to as a pencil) and the power cable and/or smoke evacuation hose typically enter into the opposite end of the hand piece. As the physician manipulates the electrosurgical instrument during a surgical procedure, the weight of the power cable and/or smoke evacuation hose continually pulls on the end of the electrosurgical instrument to which it is attached. More specifically, as the physician moves his or her wrist or adjusts the orientation of the electrosurgical instrument with his or her fingers so as to bring the electrode into contact with the patient's tissue, the weight of the power cable and/or smoke evacuation hose resists the physician's movement. The constant resistance or drag created by the power cable and/or smoke evacuation hose can cause the physician to become fatigued during a surgical procedure that requires extensive and continual use of the electrosurgical instrument.

Additionally, many electrosurgical procedures are performed on very sensitive parts of the body, such as on or around the eyes. When performing such procedures, the physician must control the movements of the electrode with great precision and accuracy. The resistance or drag created by the power cable and/or smoke evacuation hose can make it more difficult for the physician to be as precise and accurate. For instance, when moving the electrosurgical instrument to make a delicate incision, the physician must accurately compensate for the resistance from the power cable and/or smoke evacuation hose. If the physician overcompensates, an incision that is too deep or too long can result. Alternatively, if the physician undercompensates, multiple passes may be required to achieve the desired incision. Furthermore, the fatigue caused by the resistance from the power cable and/or smoke evacuation hose can adversely affect the physician's ability to accurately compensate for the resistance from the power cable and/or smoke evacuation hose.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Generally, the present invention relates to hand pieces that facilitate the performance of various procedures while reducing the amount of fatigue experienced by users performing the procedures. For instance, in one embodiment, an electrosurgical instrument includes a hand piece that holds an electrode tip in one end thereof. The hand piece is connected to an electrosurgical generator by way of an electrical cable. In contrast to most electrosurgical instruments that have an electrical cable connected to an end of the hand piece, the electrosurgical instrument of the present invention provides for the electrical cable to be connected to the hand piece at a central portion of the hand piece. The central connection location of the electrical cable to the hand piece reduces the resistance to the movement of the electrosurgical instrument created by the weight of the electrical cable. The reduced resistance leads to less fatigue in the physician's hand during electrosurgery. In addition to the central connection location between the hand piece and the electrical cable, the hand piece can be configured to allow the physician to adjust the location on the hand piece at which the electrical cable exits the hand piece. The physician can, therefore, adjust the electrical cable relative to the hand piece in order to customize the electrosurgical instrument to the physician's liking.

According to one aspect of one exemplary configuration of the present invention, the electrosurgical instrument includes an electrical cable that can be coupled to an electrosurgical generator to transmit the electrical energy from the electrosurgical generator to the hand piece of the electrosurgical instrument. The hand piece has a proximal end, a distal end, and a central portion disposed therebetween. A conductive electrode tip can be received within the distal end of the hand piece for transmitting the electrical energy from the hand piece to the tissue of a patient. The central portion of the hand piece has a receptacle configured to receive therein an end of the electrical cable. In addition, the hand piece further includes a channel system that enables a user of the electrosurgical instrument to selectively position at least a portion of the electrical cable within the channel system to thereby select an exit location from the channel system for the electrical cable.

In one exemplary embodiment, the channel system includes first and second opposing side channels and a longitudinal channel. The first and second opposing side channels extend from the receptacle to opposing sides of the hand piece. The first and second opposing side channels are configured to selectively and removably receive at least a portion of the electrical cable therein such that the electrical cable may exit the channel system from the central portion and on either side of the hand piece.

The longitudinal channel extends from the receptacle toward the proximal end of the hand piece. The longitudinal channel comprises a plurality of detents spaced along a length of the longitudinal channel and which are configured to selectively and removably receive at least a portion of the electrical cable therebetween. The plurality of detents defines a plurality of discrete exit locations from which the electrical cable can exit the channel system. The user of the electrosurgical instrument can selectively position the electrical cable within the longitudinal channel or the side channels to select the exit location of the electrical cable from the channel system.

According to other exemplary embodiments of the present invention, the channel system formed in the hand piece can include fewer or more channels. The channel system can be formed with one or more side channels, one or more longitudinal channels, or a combination thereof. Additionally, the channel system can be formed with one or more channels that can be employed with an evacuation hose that is associated with the electrosurgical instrument. The evacuation hose channels can be configured to selectively receive and retain a portion of the evacuation hose such that a user of the electrosurgical instrument can selectively adjust the exit location of the evacuation hose from the channel system.

In yet another exemplary embodiment of the present invention, an electrosurgical instrument is provided for use during an electrosurgical procedure. The electrosurgical instrument includes a hand piece and a utility conduit configured to transmit electrical energy from an electrosurgical generator to the hand piece and to convey smoke away from a surgical site. The hand piece includes a proximal end and a distal end that has an intake therein. A receptacle is disposed in the hand piece between the proximal end and the distal end and is configured to have the utility conduit connected thereto. An input device is configured to selectively control an operation of the electrosurgical instrument. Additionally, a channel system is formed in the hand piece and is configured to selectively receive and retain therein at least a portion of the utility conduit. The channel system enables an exit location of the utility conduit from the channel system to be selectively adjusted such that the exit location may be selectively moved along a length of the hand piece between the receptacle and the proximal end.

In another exemplary embodiment, an electrosurgical instrument is provided for use during an electrosurgical procedure to transmit electrical energy from an electrosurgical generator to tissue of a patient and to remove smoke from a surgical site. The electrosurgical instrument includes a utility conduit. The utility conduit includes an electrical cable configured to transmit the electrical energy from the electrosurgical generator and a smoke evacuation hose configured to convey the smoke away from the surgical site. The electrosurgical instrument also includes a hand piece having a proximal end, a distal end, and a central portion disposed therebetween. The central portion has a receptacle to which the utility conduit is connected. The hand piece also includes a channel system configured to selectively receive and retain therein at least a portion of the utility conduit. The channel system enables a user of the electrosurgical instrument to select an exit location for the utility conduit along at least a portion of the length of the hand piece.

In still a further embodiment of the present invention, a medical instrument is provided for use during an electrosurgical procedure to convey smoke away from a surgical site. The medical instrument includes a utility conduit that has a smoke evacuation hose configured to convey smoke away from a surgical site. The medical instrument also includes a hand piece having a proximal end, a distal end having an intake, and a central portion disposed between the proximal and distal ends. The central portion has a receptacle to which the smoke evacuation hose is connected. The smoke evacuation hose is in fluid communication with the intake. The hand piece further includes a channel system that enables at least a portion of the utility conduit to be selectively positioned within the channel system to thereby select an exit location from the channel system for the utility conduit. The channel system enables the exit location to be selectively adjusted such that the exit location may be selectively moved along a length of the hand piece between the receptacle and the proximal end.

Another exemplary embodiment of the present invention includes a hand-held instrument that has a hand piece and a utility conduit connected thereto and extending therefrom. The hand piece includes a proximal end and a distal end. A receptacle is disposed between the proximal end and the distal end and is configured to have the utility conduit connected thereto. A channel system is configured to selectively receive and retain therein at least a portion of the utility conduit. The channel system enables an exit location of the utility conduit from the channel system to be selectively adjusted such that the exit location may be selectively moved along a length of the hand piece between the receptacle and the proximal end.

Still another exemplary embodiment of the present invention includes a hand-held instrument having a hand piece and a utility conduit connected thereto and extending therefrom. The hand piece includes a proximal end, a distal end, and a central portion disposed approximately midway between the proximal end and the distal end. A receptacle is disposed between the distal end and the central portion and is configured to have the utility conduit connected thereto. The utility conduit extends away from the hand piece at an exit location that is disposed at about the central portion of the hand piece or between the central portion and the distal end of the hand piece.

This Brief Summary is provided to introduce a selection of concepts in a simplified form that are further described below in the Detailed Description. This Brief Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present invention relates to hand-held instruments or hand pieces that facilitate the performance of various procedures while reducing the amount of fatigue experienced by users performing the procedures. In some embodiments a hand-held instrument or hand piece is an electrosurgical instrument that holds an electrode tip in one end thereof. The hand piece is connected to a utility conduit. In embodiments that include an electrode tip, the utility conduit may include an electrical cable that is connected to an electrosurgical generator. The utility conduit may also or alternatively include a smoke/fluid evacuation hose that is connected to a vacuum device. Further, the utility conduit may include other tubes, cables, or the like for conveying electrical signals, smoke, fluid, and the like to or from the electrosurgical instrument.

In contrast to most electrosurgical instruments that have an electrical cable and/or a smoke/fluid evacuation hose connected to an end of the hand piece, the electrosurgical instrument of the present invention provides for the utility conduit to be connected to the hand piece at a central portion of the hand piece. The central connection location of the utility conduit to the hand piece reduces the resistance to the movement of the electrosurgical instrument created by the weight/moment-arm effect and drag of the utility conduit. The reduced resistance leads to less fatigue in the physician's hand and arm during electrosurgery. In addition to the central connection location between the hand piece and the utility conduit, the hand piece can be configured to allow the physician to adjust the location on the hand piece at which the utility conduit exits the hand piece. The physician can, therefore, selectively adjust the utility conduit relative to the hand piece in order to customize the electrosurgical instrument to the physician's liking.

Figure 1:
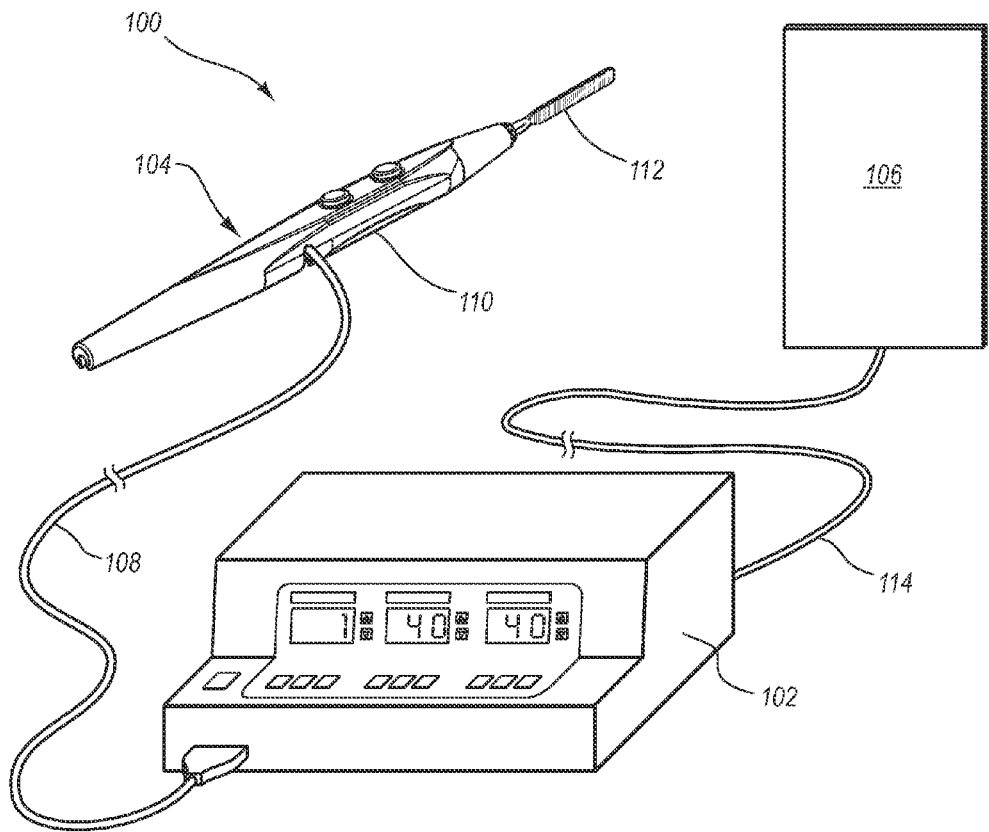
FIG. 1 illustrates an electrosurgical system with an electrosurgical instrument according to one exemplary embodiment of the present invention.

Referring to FIG. 1, an exemplary environment is illustrated that provides one operating environment for use of the present invention. In FIG. 1, an electrosurgical system 100 is illustrated, which includes a signal generator 102, an electrosurgical instrument 104, and a return electrode 106. Generator 102, in one embodiment, is an RF wave generator that produces RF electrical energy and communicates the RF electrical energy to electrosurgical instrument 104 via cable 108. Cable 108 may be considered an example or component of a utility conduit. Electrosurgical instrument 104 includes a hand piece or pencil 110 and an electrode tip 112. Electrosurgical instrument 104 communicates the RF electrical energy to a patient to cut tissue and/or cauterize blood vessels of the patient's body. Specifically, an electrical discharge is delivered from tip 112 to the patient in order to cause the heating of cellular matter of the patient that is in extremely close contact to tip 112. The heating takes place at an appropriately high temperature to allow electrosurgical instrument 104 to be used to perform electrosurgery. Return electrode 106 and cable 114 provide a return electrical path to wave generator 102 for any excess charge that dissipated into surrounding tissue of the patient's body.

Figure 2:
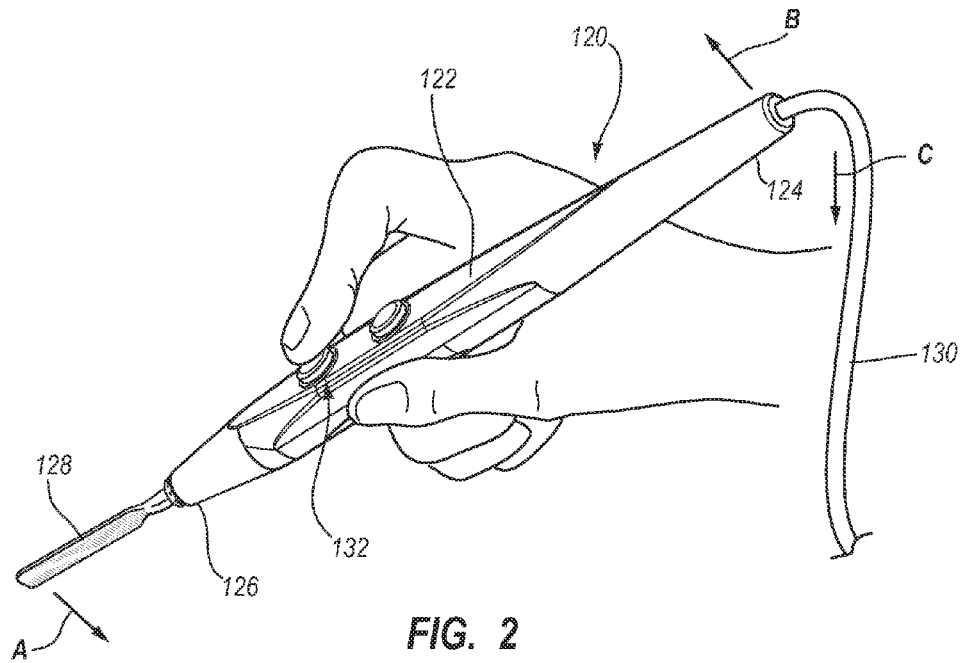
FIG. 2 illustrates one manner of holding an electrosurgical instrument.

Illustrated in FIG. 2 is an electrosurgical instrument 120 commonly used to perform electrosurgical procedures. Electrosurgical instrument 120 includes a hand piece 122 having a proximal end 124 and a distal end 126. An electrode tip 128 is received within distal end 126. A cable 130 is connected to electrosurgical instrument 120 at proximal end 124. Cable 130 communicates electrical energy from an electrosurgical generator, such as generator 102 in FIG. 1, to electrosurgical instrument 120. The electrical energy is passed through electrode tip 128 and into a patient's tissue.

Electrosurgical instruments, such as electrosurgical instrument 120, are commonly referred to as electrosurgical pencils or pens because in use they are often held in the same manner as a pencil or pen when writing. FIG. 2 illustrates one of the most common manners by which physicians hold electrosurgical instrument 120 during an electrosurgical procedure. As can be seen, hand piece 122 is laid through the crook of the hand and is held in place by the middle finger and thumb. The index finger is placed on top of hand piece 122 to further hold hand piece 122 in place as well as to activate input device 132.

As noted elsewhere herein, the flexibility, weight/moment-arm and drag characteristics of cable 130 and the connection location of cable 130 to hand piece 122 limit the ability of the physician during a surgical procedure. While holding electrosurgical instrument 120 as shown in FIG. 2, a physician will perform electrosurgery by activating input device 132 and moving electrode tip 128 into contact with the patient's tissue. To make contact between electrode tip 128 and the patient's tissue, the physician will move his or her wrist or fingers to adjust the position and/or orientation of electrosurgical instrument 120.

For instance, the physician may move his or her wrist so that electrode tip 128 moves in the direction of arrow A toward the patient's tissue. Notably, as the physician moves electrode tip 128 in the direction of arrow A, proximal end 124 moves in the direction of arrow B. The weight of cable 130 constantly pulls proximal end 124 in the direction of arrow C. Thus, the weight of cable 130 resists the movement of proximal end 124 in the direction of arrow B.

The resistance created by the weight of cable 130 is accentuated by the location at which cable 130 is connected to hand piece 122. As is understood, a torque is created by applying a force at a distance from an axis or pivot point. The magnitude of the torque is a result of the magnitude of the applied force and the distance between the axis/pivot point and the location where the force is applied. In the case of electrosurgical instrument 120, the weight of cable 130 is the force that contributes to the generation of the resistive torque. Additionally, the location at which cable 130 attaches to hand piece 122 and how hand piece 122 is held creates the lever arm through which the weight of cable 130 works to create the torque. More specifically, cable 130 enters hand piece 122 at or near proximal end 124. When electrosurgical instrument 120 is held as shown in FIG. 2, proximal end 124 is positioned above and away from the crook of the physician's hand, which acts as the pivot point. The weight of cable 130 pulls down on proximal end 124, thereby creating a torque or moment-arm. Because the magnitude of the torque is dependent on the distance between the pivot point and the force, the further apart the connection point between cable 130 and hand piece 122 is away from the crook of the hand, the greater the torque will be. Understandably, the larger the torque is, the greater amount of resistance the physician will experience when manipulating electrosurgical instrument 120.

To overcome the resistance created by the weight of cable 130, the physician must exert additional energy to move electrosurgical instrument 120 into the desired orientation. Continuously working against the resistance created by cable 130 can cause the physician's hand, and/or wrist, and/or arm to become fatigued during an electrosurgical procedure. This fatigue can also lead to a loss of accuracy and precision in the performance of the procedure.

Attention is now directed to FIGS. 3-8, which illustrate embodiments of electrosurgical instruments which reduce the resistance created by the electrical cable that connects the electrosurgical instruments to an electrosurgical generator. The embodiments shown in FIGS. 3-8 include a connection point between the electrical cable and the hand piece that is more centrally located between the proximal and distal ends of the hand piece. Additionally, the hand pieces can include one or more grooves or channels into which the cable can be received. The grooves/channels and/or cable can be configured to allow a physician to select the point at which the cable will extend from the hand piece, referred to hereinafter as the "exit location" of the cable. By allowing the physician to select and adjust the exit location, the physician is able to reduce or eliminate the resistance created by the weight of the cable, which can reduce the fatigue experienced during an electrosurgical procedure.

Figure 3:
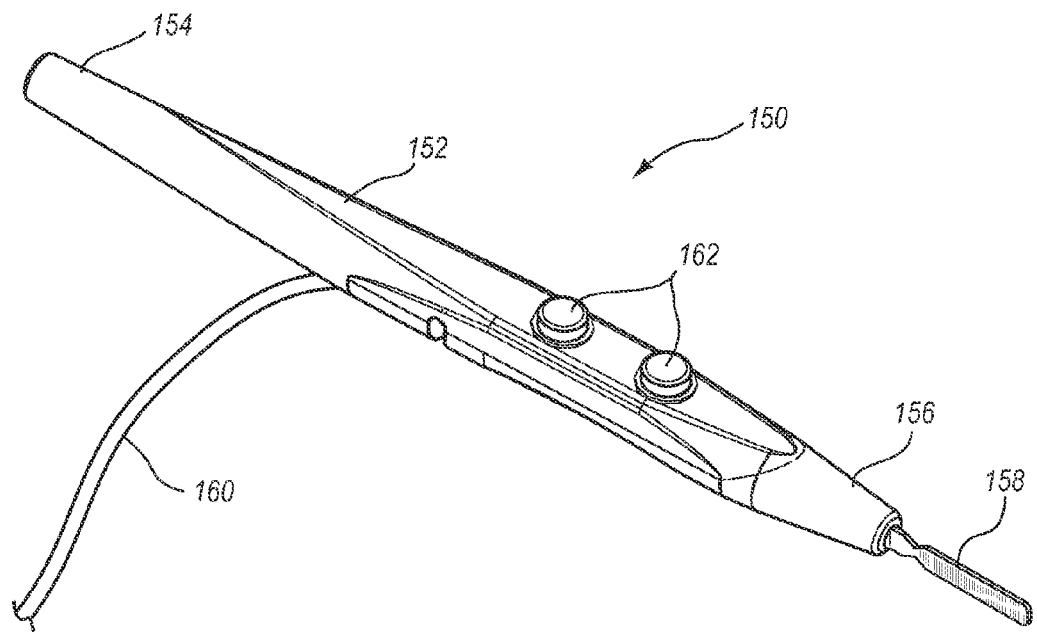
FIG. 3 is a perspective view of an electrosurgical instrument according to an exemplary embodiment of the present invention.
Figure 4:
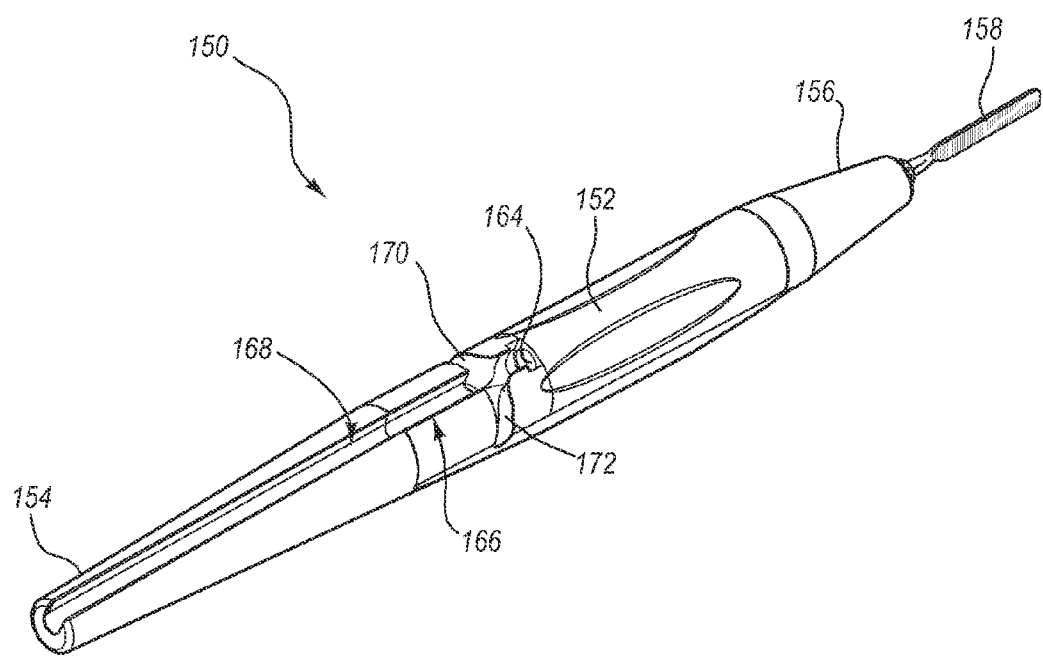
FIG. 4 is a bottom perspective view of the electrosurgical instrument of FIG. 3 showing a channel system formed in a hand piece thereof.
Figure 5:
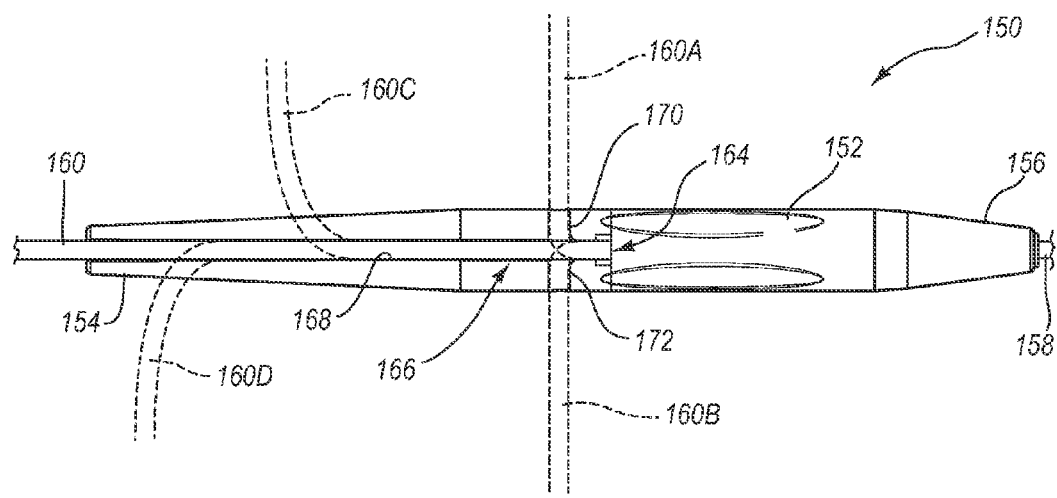
FIG. 5 is a bottom view of the electrosurgical instrument of FIG. 3 showing exemplary exit locations for an electrical cable that is connected to the hand piece of the electrosurgical instrument.

For example, FIGS. 3-5 illustrate one exemplary embodiment of an electrosurgical instrument 150 according to the present invention. Electrosurgical instrument 150 includes a hand piece 152 having a proximal end 154 and a distal end 156. Distal end 156 is configured to receive an electrode tip 158. Hand piece 152 is connected to cable 160, which delivers electrical energy from a generator, such as generator 102 in FIG. 1, to electrode tip 158. Hand piece 152 also includes input devices 162 for controlling the flow of electrical energy to electrode tip 158. As can be seen in FIG. 3, cable 160 extends from a central portion of hand piece 152 as opposed to extending from the proximal end of the hand piece as cable 130 does in FIG. 2.

FIG. 4 illustrates a bottom perspective view of electrosurgical instrument 150. As seen therein, hand piece 152 includes a receptacle 164. An end of cable 160 (not shown in FIG. 4) is inserted into receptacle 164 and connected to the internal components of hand piece 152 to provide electrical energy to electrode tip 158. Hand piece 152 also includes a channel system 166 that allows a physician to select the exit location of cable 160. In other words, while cable 160 is connected to hand piece 152 at receptacle 164, a portion of cable 160 can be positioned within channel system 166 so that cable 160 exits or extends from hand piece 152 at any one of a number of locations on hand piece 152, whether adjacent to or distant from receptacle 164.

In the exemplary embodiment illustrated in FIG. 4, channel system 166 includes a longitudinal channel 168 and opposing side channels 170 and 172. Each of channels 168, 170, and 172 begins near and extends away from receptacle 164. Longitudinal channel 168 generally extends in a straight line from receptacle 164 to proximal end 154. Opposing side channels 170 and 172 extend from receptacle 164 and out opposing sides of hand piece 152. Channels 168, 170, and 172 are each sized to selectively receive and retain at least a portion of cable 160 therein.

FIG. 5 depicts cable 160 exiting or extending away from hand piece 152 at various possible locations. For the sake of clarity, cable 160 is identified in FIG. 5 with reference numbers 160, 160A, 160B, 160C, and 160D. While references numbers 160, 160A, 160B, 160C, and 160D identify the same cable 160, the reference letters A, B, C, and D are used to aid in the following description of cable 160 exiting or extending from hand piece 152 at different locations. Similar lettering is also used elsewhere herein with reference to cables 192, 210, and 222 and utility conduit 260.

As shown in FIG. 5, cable 160A can extend out of receptacle 164 and be positioned in channel 170 so that cable 160A extends out of the right side of hand piece 152 (when viewed from the top of hand piece 152). As noted above, channel 170 can be sized to snuggly retain cable 160A therein so that cable 160A does not inadvertently come out of channel 170 while electrosurgical instrument 150 is being used. Positioning cable 160A in channel 170 so that cable 160A exits hand piece 152 on the right side may be particularly comfortable for a left-handed physician. When cable 160A is positioned within channel 170, a left-handed physician may hold hand piece 152 so that cable 160A extends out of the right side of hand piece 152 towards the physician's thumb. The physician may allow cable 160A to extend in a downward direction below the thumb. Alternatively, the physician may position cable 160A so that it extends over the top of the thumb before extending in a downward direction.

Similarly, cable 160B can extend out of receptacle 164 and be positioned in channel 172 so that cable 160B extends out of the left side of hand piece 152 (when viewed from the top of hand piece 152). As with channel 170, channel 172 can be sized to snuggly retain cable 160B therein so that cable 160B does not inadvertently come out of channel 172 while electrosurgical instrument 150 is being used. Positioning cable 160B in channel 172 so that cable 160B exits hand piece 152 on the left side may be particularly comfortable for a right-handed physician. A right-handed physician holding hand piece 152 with cable 160B positioned within channel 172 can allow cable 160B to extend below or over the top of the thumb in the same manner as described above with reference to cable 160A and channel 170.

Positioning cable 160A/160B within channel 170/172, as shown in FIG. 5, significantly reduces or eliminates the resistance typically created by the electrical cable, as described above with reference to FIG. 2. When cable 160A/160B is positioned within channel 170/172, the exit location of cable 160A/160B is relatively close to the crook of the physician's hand. This positioning of the exit location for cable 160A/160B reduces the torque created by the cable. Specifically, because the distance between the applied force (i.e., the weight of the cable) and the pivot point (i.e., the crook of the hand) is relatively small, the torque created by cable 160A/160B is much smaller than the torque created by cable 130 described above with reference to FIG. 2. Due to the smaller torque, a physician will experience less resistance and fatigue when using electrosurgical instrument 150 with cable 160A/160B positioned within channel 170/172 as compared to a typical electrosurgical instrument in which the cable is connected at the proximal end.

Some physicians may prefer to have cable 160 exit hand piece 152 at a location other than those provided by channels 170 and 172. In such a case, the physician may use channel 168 to achieve a comfortable exit location for cable 160. To achieve a comfortable exit location, a physician may position a portion of cable 160 within channel 168 so that cable 160 extends from receptacle 164, through channel 168, and exits channel 168 at a desired location between receptacle 164 and proximal end 154.

For instance, with reference to cable 160C of FIG. 5, the physician may position about one or two inches of cable 160C within channel 168 and then allow the remainder of cable 160C to remain free from hand piece 152. In such a case, cable 160C may exit hand piece 152 so that cable 160C lies in the crook of the hand and then falls in a downward direction near the physician's wrist. Alternatively, with reference to cable 160D of FIG. 5, the physician may position between about two and three inches of cable 160D within channel 168 and then allow the remainder of cable 160D to remain free from hand piece 152. In yet other situations, the physician may position cable 160 through the entire length of channel 168 so that cable 160 does not exit hand piece 152 until proximal end 154.

While five exit locations have been illustrated in FIG. 5, one associated with each of cables 160, 160A, 160B, 160C, and 160D, it will be readily understood that channel system 166 can provide still other exit locations for an electrical cable. Channel system 166 is configured to allow a physician to select any location along the length of channel 168 as an exit location. For instance, a physician with a larger hand may desire cable 160 to exit closer to proximal end 154. This can be accomplished by simply positioning more of cable 160 within channel 168 so that the exit location of cable 160 is closer to proximal end 154. Alternatively, a physician with a smaller hand may desire cable 160 to exit very near receptacle 164. This can be accomplished using channels 170 and 172 or by positioning only a short length of cable 160 within channel 168. Thus, channel system 166 allows a physician to customize hand piece 152 so that hand piece 152 is most comfortable to that physician and reduces the resistance and fatigue caused by cable 160.

Figure 6:
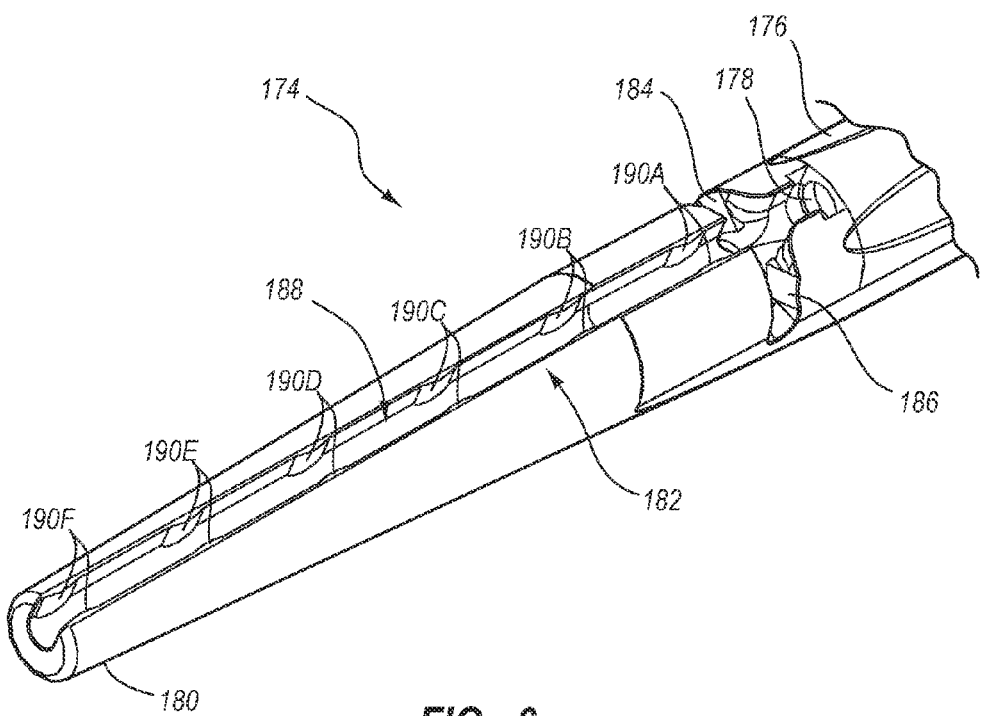
FIG. 6 is a bottom perspective view of a another exemplary embodiment of an electrosurgical instrument having a channel system.
Figure 7:
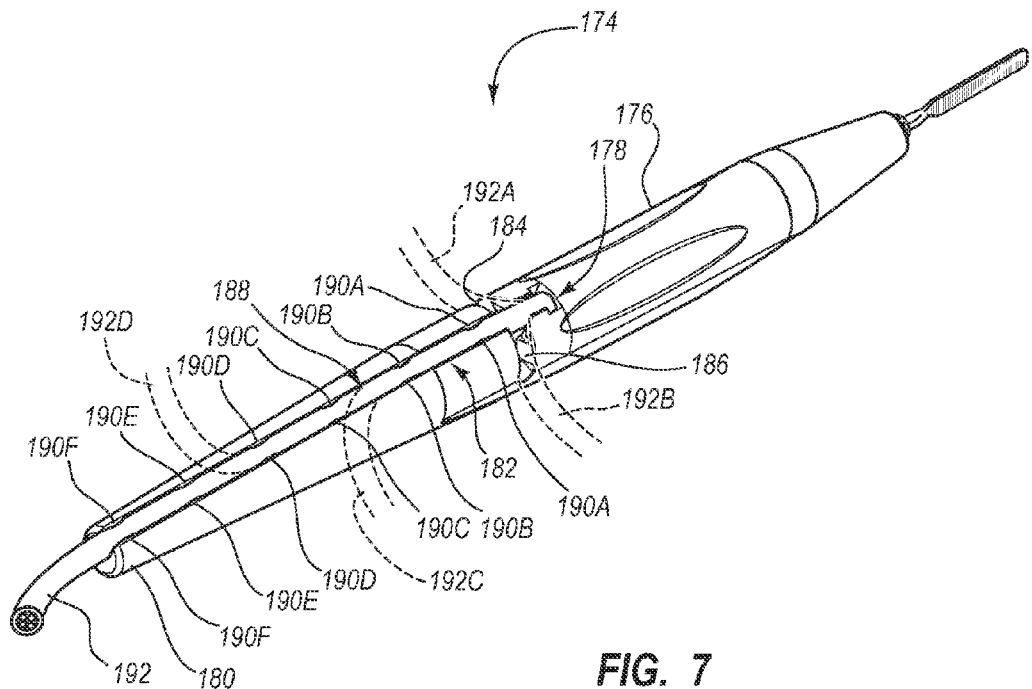
FIG. 7 is a bottom perspective view of the electrosurgical instrument of FIG. 6 showing exemplary exit locations for an electrical cable that is connected to the hand piece of the electrosurgical instrument.

Turning attention now to FIGS. 6 and 7, there is illustrated an alternative embodiment of a channel system that can be incorporated into an electrosurgical instrument. With specific reference to FIG. 6, there is shown an electrosurgical instrument 174 that includes a hand piece 176. Hand piece 176 includes a receptacle 178. An end of cable 192 (FIG. 7) is inserted into receptacle 178 and connected to the internal components of hand piece 176 to provide electrical energy to an electrode tip.

Hand piece 176 also includes a channel system 182 similar to channel system 166. Specifically, channel system 182 includes opposing side channels 184 and 186 and a longitudinal channel 188. Opposing side channels 184 and 186 are generally the same as channels 170 and 172 described above. Channel 188 is also similar to channel 168. Channel system 182 allows a physician to select the exit location of cable 192 in much the same manner as described above with reference to channel system 166. More particularly, a physician may select the exit location of cable 192 by positioning cable 192 within one of channels 184, 186, 188. Selection of channels 184 and 186 causes cable 192 to exit the sides of hand piece 176, similar to cable 160 exiting the sides of hand piece 152 through channels 170 and 172. In the case of using channel 188, the physician can also select from a number of predefined exit locations along the length of channel 188. Thus, channel system 182 allows a physician to customize electrosurgical instrument 174 so as to reduce the resistance and fatigue caused by cable 192 and make electrosurgical instrument 174 more comfortable to use.

While channel 188 is similar to channel 168, channel 188 further includes detents 190A, 190B, 190C, 190D, 190E, and 190F, collectively referred to as detents 190. Each of detents 190A, 190B, 190C, 190D, 190E, and 190F includes two opposing ridges positioned within channel 188. Detents 190 are configured to selectively receive and retain cable 192 therebetween. Thus, a physician may position cable 192 within channel 188 and between one or more of detents 190A, 190B, 190C, 190D, 190E, and 190F so as to hold cable 192 while the physician uses electrosurgical instrument 174.

Channel 168, described above, allows a physician to select an exit location anywhere along the length of channel 168. In contrast, detents 190 create a plurality of discrete exit locations for cable 192 along the length of channel 188. In other words, detents 190 provide a physician with the option of selecting an exit location from multiple, predefined exit locations.

As noted, detents 190 are configured to selectively retain cable 192 therebetween. The areas of channel 188 between detents 190 can be configured to allow cable 192 to exit channel 188 when subsequent detents 190A, 190B, 190C, 190D, 190E, and/or 190F are not employed to retain cable 192 within channel 188. For example, as illustrated in FIG. 7, a physician may position cable 192C within channel 188 so that cable 192C extends between detents 190A and 190B, but not between detents 190C, 190D, 190E, and 190F. In such a case, cable 192C is then able to exit channel 188 between detents 190B and 190C. Thus, the area between detents 190B and 190C constitutes one of the plurality of discrete exit locations for cable 190. Similarly, the physician may position cable 192D within channel 188 so that cable 192D extends between detents 190A, 190B, 190C, and 190D, but not between detents 190E and 190F. In such a case, cable 192D is then able to exit channel 188 between detents 190D and 190E. Thus, the area between detents 190D and 190E constitutes another one of the plurality of discrete exit locations for cable 190. The areas between detents 190A and 190B, 190C and 190D, and 190E and 190F can similarly constitute discrete exit location for cable 190. While channel 188 is illustrated in FIGS. 6 and 7 with six detents 190 and five exit locations, it will be understood that a channel system can be formed with fewer or more than six detents 190 and five exit locations.

Channel system 182 therefore provides a physician with the ability to customize electrosurgical instrument 174 in order to reduce the resistance and fatigue caused by cable 192. Additionally, channel system 182 also allows the physician to adjust the exit location of cable 192 to make electrosurgical instrument 174 more comfortable for the physician.

Figure 8:
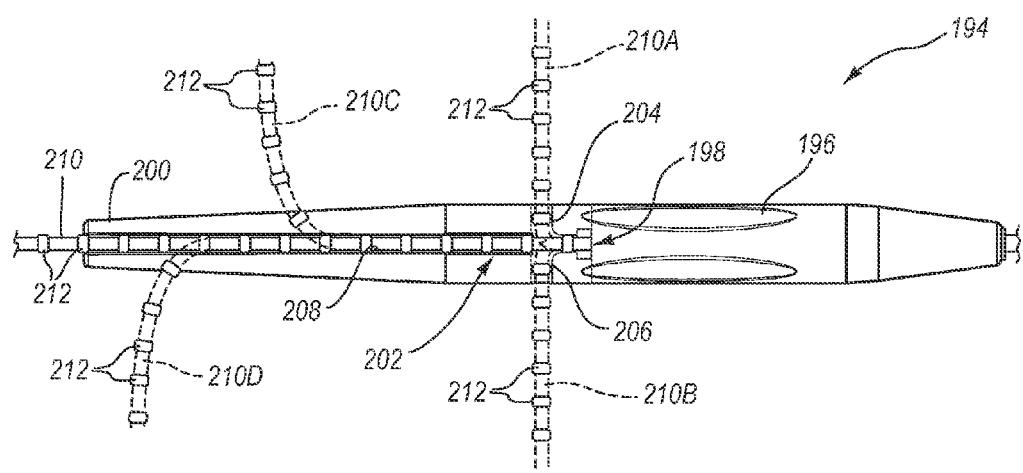
FIG. 8 is a bottom perspective view of yet another exemplary embodiment of an electrosurgical instrument having a channel system.

FIG. 8 illustrates yet another embodiment of an electrosurgical instrument 194 that reduces the resistance and fatigue caused by the weight and connection location of a cable to the hand piece. In the illustrated embodiment, electrosurgical instrument 194 includes a hand piece 196 having a receptacle 198, a proximal end 200, and a channel system 202. As with receptacles 164 and 178, receptacle 198 is configured to receive an end of cable 210, which provides electrical energy to an electrode tip. Channel system 202 is generally the same as channel system 166. In particular, channel system 202 includes opposing side channels 204 and 206 and a longitudinal channel 208, each of which is sized and configured to selectively receive and retain cable 210 therein.

As with the previous channel systems described herein, channel system 202 allows a physician to select the exit location of cable 210, thereby making electrosurgical instrument 194 more comfortable and reducing the resistance created by the cable. In the present embodiment, however, cable 210 includes a plurality of detents 212 on its outer surface and along its length. Detents 212 provide similar functionality as detents 190 described above. In particular, detents 212 can be sized to snuggly fit within channels 204, 206, and 208 so that cable 210 is retained therein. In addition, detents 212 can be used to select how much of cable 210 is retained within channel system 202. For instance, a physician may position cable 210C within channel 208 so that six detents 212 are held within channel 208, and the remainder of cable 210C is able to hang freely out of channel 208. Alternatively, the physician may position more detents 212 of cable 210 within channel 208, as shown with cable 210D, so that the exit location of cable 210 is closer to proximal end 200. In this manner, the physician may again select from a plurality of predefined, discrete exit location for cable 210, similar to the predefined, discrete exit locations discussed with reference to FIGS. 6 and 7. In this case, however, the predefined, discrete exit locations are created by detents 212 on cable 210 rather than detents 190 formed in the channel system.

Figure 9:
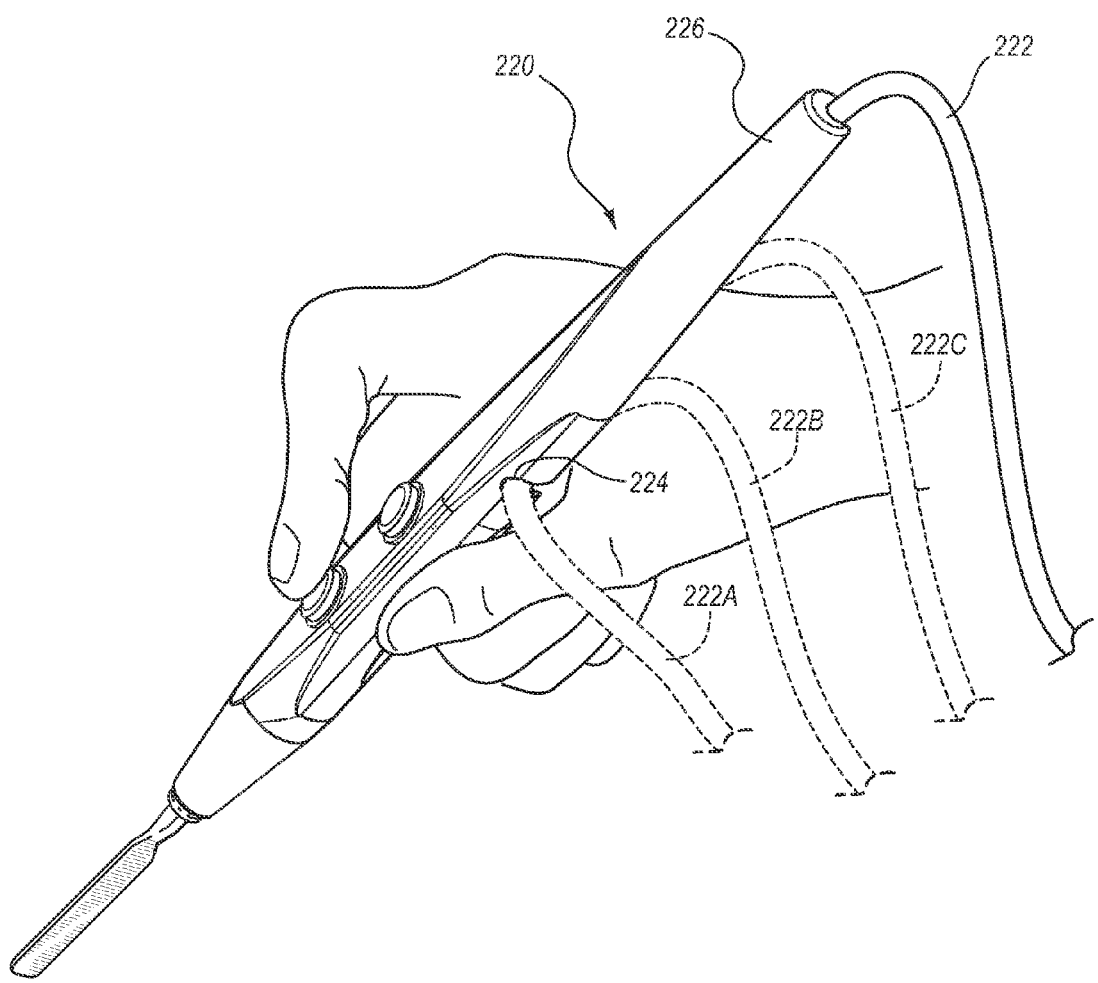
FIG. 9 illustrates an exemplary electrosurgical instrument being held with the electrical cable exiting the electrosurgical instrument from multiple exemplary exit locations.

FIG. 9 illustrates an electrosurgical instrument 220. Electrosurgical instrument 220 can incorporate any one of the channel systems and/or cables/hoses 222 described herein. FIG. 9 illustrates a few examples of where and how a cable or hose 222 exits the electrosurgical instrument 220 and falls relative to a physician's hand. For instance, cable 222A exits electrosurgical instrument 220 through a side channel 224. As can be seen, cable 222A extends out of electrosurgical instrument 220 toward the physician's thumb. Alternatively, the physician can have cable 222B exit electrosurgical instrument 220 on the front side of the physician's palm so that cable 222B is positioned in the palm of the physician's hand. The physician may further select an exit location near the crook of the hand so that cable 222C extends down the crook of the hand towards the wrist. The physician may further select an exit location for cable 222D that is closer to proximal end 226. Still further, the physician may elect to have cable 222 exit electrosurgical instrument 220 at proximal end 226, similar to a standard electrosurgical instrument.

A channel system according to the present invention may also be configured to accommodate multiple cables and/or hoses commonly associated with electrosurgical instruments. For instance, in addition to an electrical cable, many electrosurgical instruments include an evacuation hose to remove smoke or fluid from a surgical site during an electrosurgical procedure. As with the electrical cables, the evacuation hoses are commonly connected to the proximal end of the hand piece, thereby creating resistance to the movement of the electrosurgical instrument. This resistance can, like the resistance from the electrical cables, cause the physician to experience fatigue during an electrosurgical procedure.

To reduce the fatigue caused by the evacuation hoses, a channel system as described herein can be incorporated in the electro surgical instrument to allow the physician to adjust the exit location of the evacuation hose. For instance, a channel system can be incorporated that allows the evacuation hose to exit the hand piece at a location closer to the physician's hand, thereby reducing the torque created by the weight of the evacuation hose. As described above, the channel system can be configured to allow the physician to select the exit location from anywhere along the length of the hand piece, or from one of a plurality of predefined, discrete exit locations.

Figure 10:
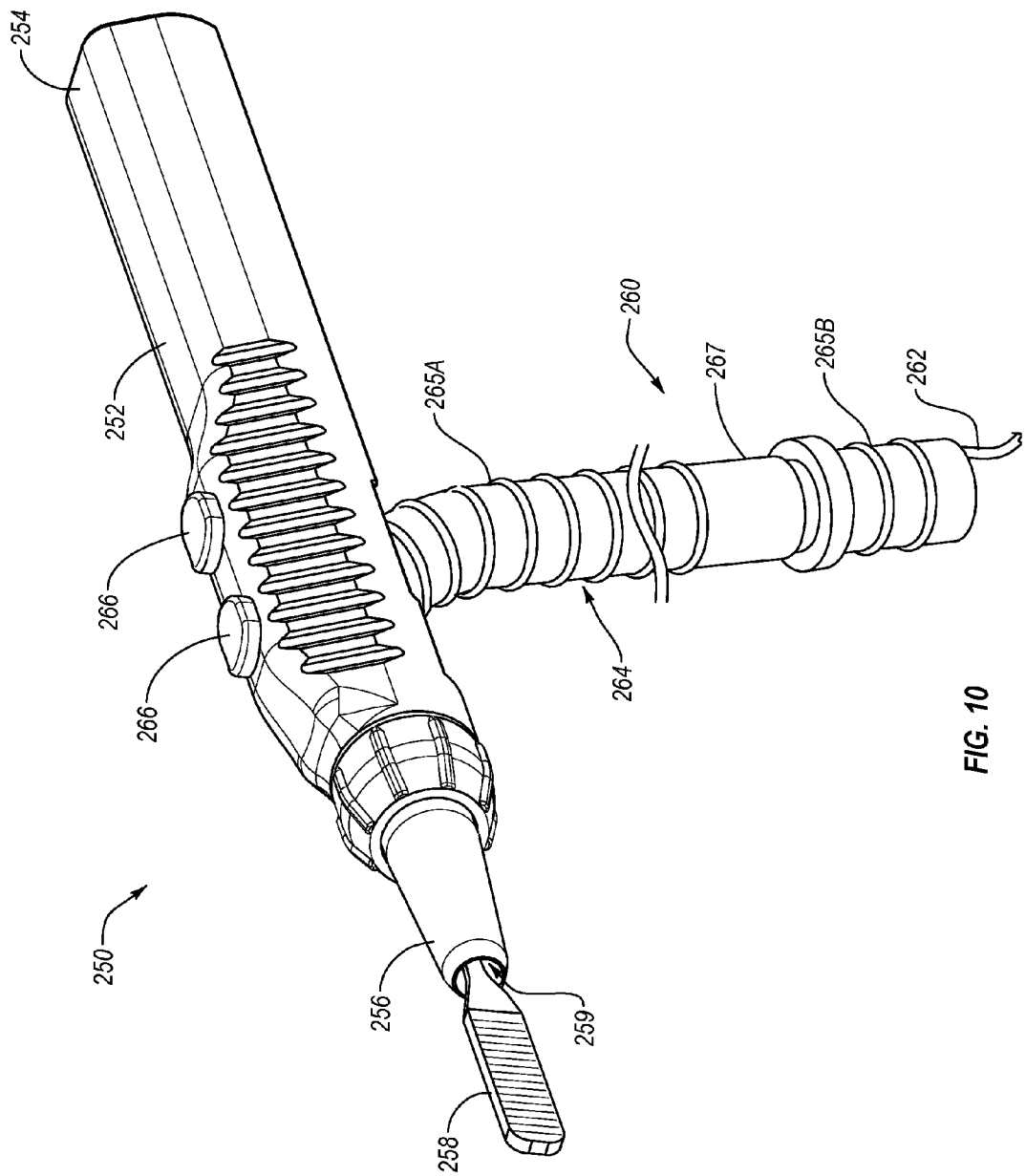
FIG. 10 is a perspective view of an electrosurgical instrument according to another exemplary embodiment of the present invention.

For example, FIGS. 10-14 illustrate another exemplary embodiment of an electrosurgical instrument 250 according to the present invention. Electrosurgical instrument 250 includes a hand piece 252 having a proximal end 254 and a distal end 256. Distal end 256 is configured as a nozzle that can receive an electrode tip 258 at least partially therein. More specifically, electrode tip 258 is received at least partially within an intake 259 of distal end 256. As can be seen in FIG. 10, there is open space between electrode tip 258 and the interior surface of intake 259 to enable smoke and/or fluids to be drawn into intake 259.

Hand piece 252 is connected to a utility conduit 260. As can be seen in FIG. 10, utility conduit 260 extends from a central portion of hand piece 252 as opposed to extending from the proximal end of the hand piece as cable 130 does in FIG. 2. In the illustrated embodiment, utility conduit 260 includes a cable 262 that delivers electrical energy from a generator, such as generator 102 in FIG. 1, to electrode tip 258.

Additionally, utility conduit 260 also includes a smoke/fluid evacuation hose 264 that conveys smoke/fluid away from a surgical site. Smoke/fluid evacuation hose 264 is connected to hand piece 252 so as to be in fluid communication with intake 259. Smoke/fluid evacuation hose 264 may be connected to a vacuum device so as to draw smoke and/or fluid into intake 259, through smoke/fluid evacuation hose 264, and away from a surgical site. Cable 262 or another cable may connect hand piece 252 to the vacuum device so that hand piece 252 may control the vacuum device.

Although utility conduit 260 is described herein as including both cable 262 and smoke/fluid evacuation hose 264, such configuration is merely exemplary. In other embodiments, such as those shown in FIGS. 3-9 for instance, a utility conduit may only include a power cable. In still other embodiment, a utility conduit may only include a smoke/fluid evacuation hose. In still other embodiments, a utility conduit may include one or more cables and/or one or more hoses.

In the illustrated embodiment, at least a portion of cable 262 is disposed within smoke/fluid evacuation hose 264. In other embodiments, however, cable 262 may be disposed entirely outside of smoke/fluid evacuation hose 264. In such embodiments, cable 262 and smoke/fluid evacuation hose 264 may optionally be connected to one another along at least a portion of their lengths.

Hand piece 252 also includes input devices 266 for controlling the flow of electrical energy to electrode tip 258 and/or evacuation of smoke and/or fluid from the surgical site.

Figure 11:
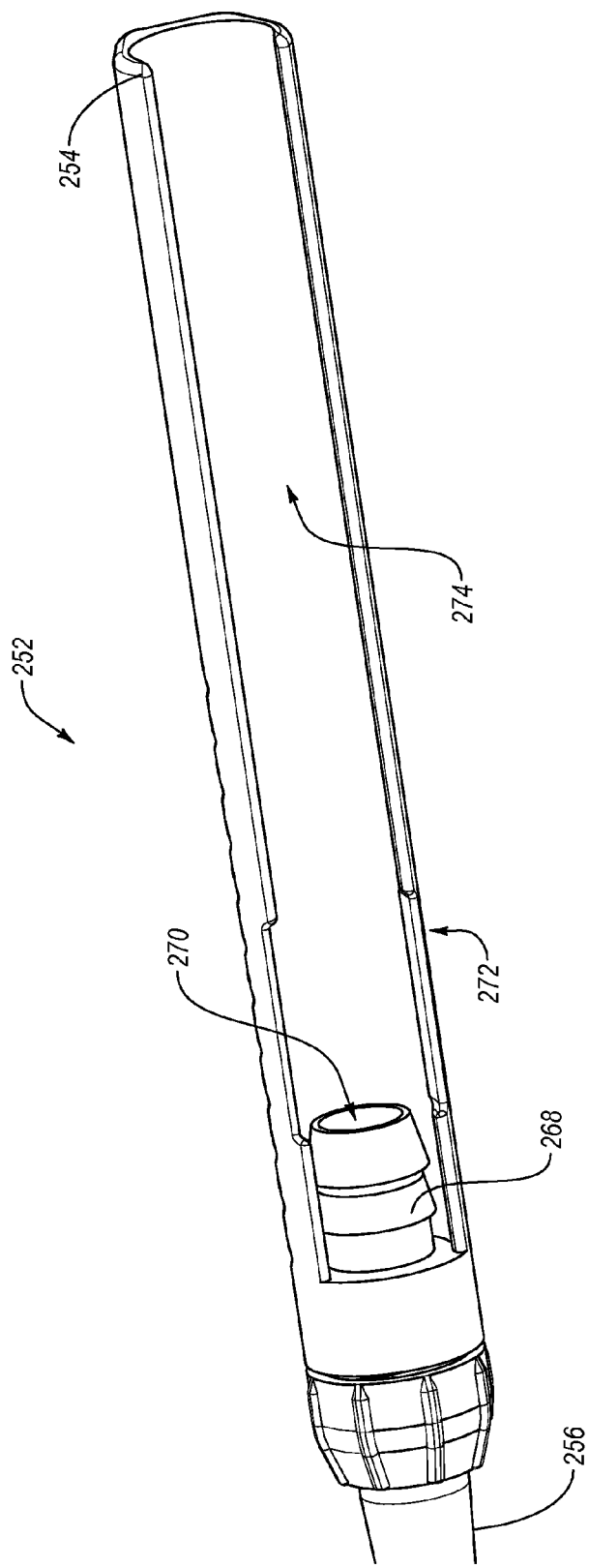
FIG. 11 is a bottom perspective view of the electrosurgical instrument of FIG. 10 with a utility conduit removed to show a channel system formed in a hand piece of the electrosurgical instrument.

FIG. 11 illustrates a bottom perspective view of hand piece 252. As seen therein, hand piece 252 includes a receptacle 268. An end of utility conduit 260 (not shown in FIG. 11) may be connected to receptacle 268. For instance, an end of smoke/fluid evacuation hose 264 may be disposed around or received within receptacle 268. As seen in FIG. 11, receptacle 268 includes a conduit 270 that is in fluid communication with intake 259. As a result, when smoke/fluid evacuation hose 264 is connected to receptacle 268, smoke/fluid evacuation hose 264 is in fluid communication with intake 259. Accordingly, smoke and/or fluid may be drawn into intake 259, passed through conduit 270, and conveyed away through smoke/fluid evacuation hose 264.

The connection between utility conduit 260 and receptacle 268 may allow for relative movement between hand piece 252 and utility conduit 260. For instance, receptacle 268 may be formed separate from hand piece 252 and later connected thereto. Even more specifically, receptacle 268 may take the form of a swivel that include a first end that may be connected to hand piece 252 and a second end that is connected to utility conduit 260. The connection between the first end of receptacle 268 and hand piece 252, the connection between the first and second ends of receptacle 268 (when formed of two or more pieces), and/or the connection between the second end of receptacle 268 and utility conduit 260 may allow for hand piece 252 to rotate relative to utility conduit 260 or vice versa. For instance, the first end of receptacle 268 may be rotationally connected to hand piece 252 to allow for relative movement between hand piece 252 and utility conduit 260. Similarly, the second end of receptacle 268 may be rotationally connected to utility conduit 260 to allow for similar relative movement between hand piece 252 and utility conduit 260. Likewise, the first and second ends of receptacle 268 may be rotationally connected together to allow for relative movement between hand piece 252 and utility conduit 260. In any case, such relative movement may reduce or eliminate longitudinal rotational torque of hand piece 252 by utility conduit 260.

In addition or as an alternative to hand piece 252 and utility conduit 260 being movably connected together (e.g., a swivel-type receptacle 268), utility conduit 260 may include two or more sections that are connected together in a manner that allows for relative movement between adjacent sections. For instance, as shown in FIGS. 10 and 12-14, utility conduit 260 may include a first section 265A and a second section 265B that are connected together via a swivel 267. Swivel 267 may include a first half and a second half that are able to rotate relative to one another. First section 265A may be connected to the first half of swivel 267 and second section 265B may be connected to the second half of swivel 267. The ability of the first and second halves of swivel 267 to rotate relative to one another enables first and second sections 265A, 265B of utility conduit 260 to also rotate relative to one another. As a result, hand piece 252 and first section 265A are able to move and rotate relative to second section 265B with less longitudinal rotational torque.

In order to efficiently convey smoke/fluid away from the surgical site, the connections between hand piece 252, receptacle 268, utility conduit 260, first and second sections 265A, 265B, and swivel 267 (and first and second halves thereof), may be substantially airtight and/or watertight.

Although not shown in FIG. 11, receptacle 268 also includes electrical connections for connecting cable 262 to hand piece 252. The electrical connection between hand piece 252 and cable 262 allows for controlling the flow of electrical energy to electrode tip 258 and/or removing smoke and/or fluid from the surgical site.

Hand piece 252 also includes a channel system 272 similar to channel systems 166, 182, and 202. Like the other channel systems described herein, channel system 272 allows a physician to select the exit location of utility conduit 260 from hand piece 252. That is, while utility conduit 260 is connected to hand piece 252 at receptacle 268, a portion of utility conduit 260 can be positioned within channel system 272 so that utility conduit 260 exits or extends from hand piece 252 at any one of a number of locations along hand piece 252, whether adjacent to or distant from receptacle 268.

In the exemplary embodiment illustrated in FIG. 11, channel system 272 includes a longitudinal channel 274. Longitudinal channel 274 begins near and extends away from receptacle 268 in a generally straight line toward proximal end 254. In other embodiments, longitudinal channel 274 and/or receptacle 268 may be arranged in other configurations. For instance, receptacle 268 may not be aligned with distal end 256 and/or channel 274 may not extend in a generally straight line toward proximal end 254. Rather, channel 274 and/or receptacle 268 may be configured in an offset alignment depending upon the device design and/or desired flow path arrangement.

Longitudinal channel 274 is sized to selectively receive and retain at least a portion of utility conduit 260 therein. That is, longitudinal channel 274 can be sized to snuggly retain utility conduit 260 therein so that utility conduit 260 does not inadvertently come out of longitudinal channel 274 while electrosurgical instrument 250 is being used. As a result of the size and configuration of longitudinal channel 274, hand piece 252 is substantially hollow between receptacle 268 and proximal end 254. For instance, in some embodiments, hand piece 252 is at least 70% hollow. More specifically, in some embodiments, longitudinal channel 274 reduces the overall volume of hand piece 252 by more than 70%. In the illustrated embodiment, for example, hand piece 252 has a width between opposing side surfaces of about 0.65 inches and longitudinal channel 274 has a width of about 0.55 inches. Accordingly, the ratio between the widths of hand piece 252 and longitudinal channel 274 is about 0.85, resulting in hand piece 252 being about 85% hollow. It will be appreciated, however, that the foregoing percentages and ratios are merely exemplary. By way of non-limiting example, a hand piece may be substantially hollow if the ratio between the width of the hand piece and the width of the longitudinal channel is greater than about 25%, about 40%, about 50%, or about 75%.

Figure 12:
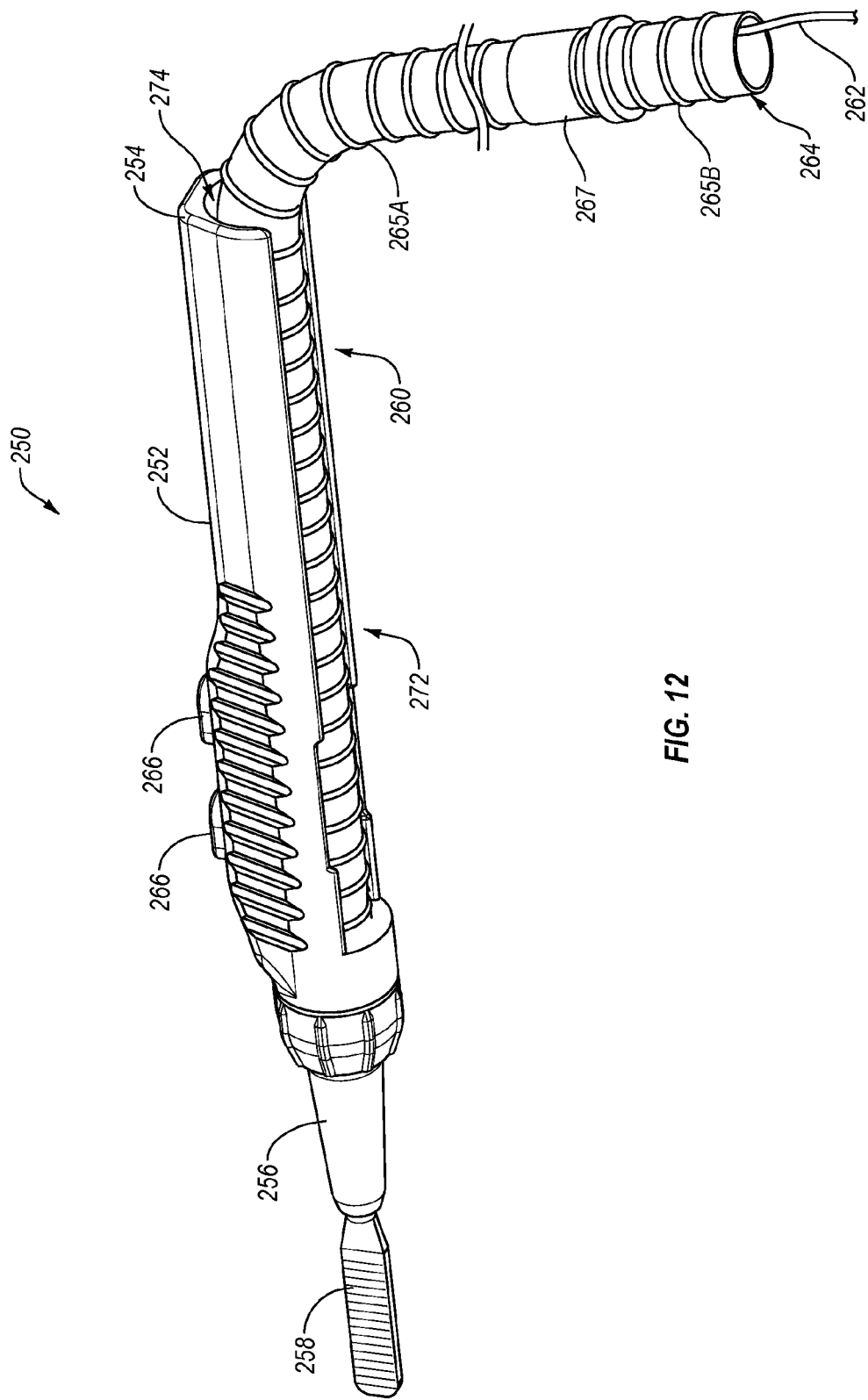
FIG. 12 is a bottom perspective view of the electrosurgical instrument of FIG. 10 showing an exemplary exit location for a utility conduit that is connected to the hand piece of the electrosurgical instrument.

FIG. 12 depicts utility conduit 260 exiting or extending away from hand piece 252 at one possible location. As shown in FIG. 12, utility conduit 260 can extend away from receptacle 268 (which is generally below input devices 266 in the illustrated embodiment) and be positioned in longitudinal channel 274. In FIG. 12, utility conduit 260 is shown disposed in the entire length of longitudinal channel 274 such that utility conduit 260 exits hand piece 252 adjacent proximal end 254.

Figure 13:
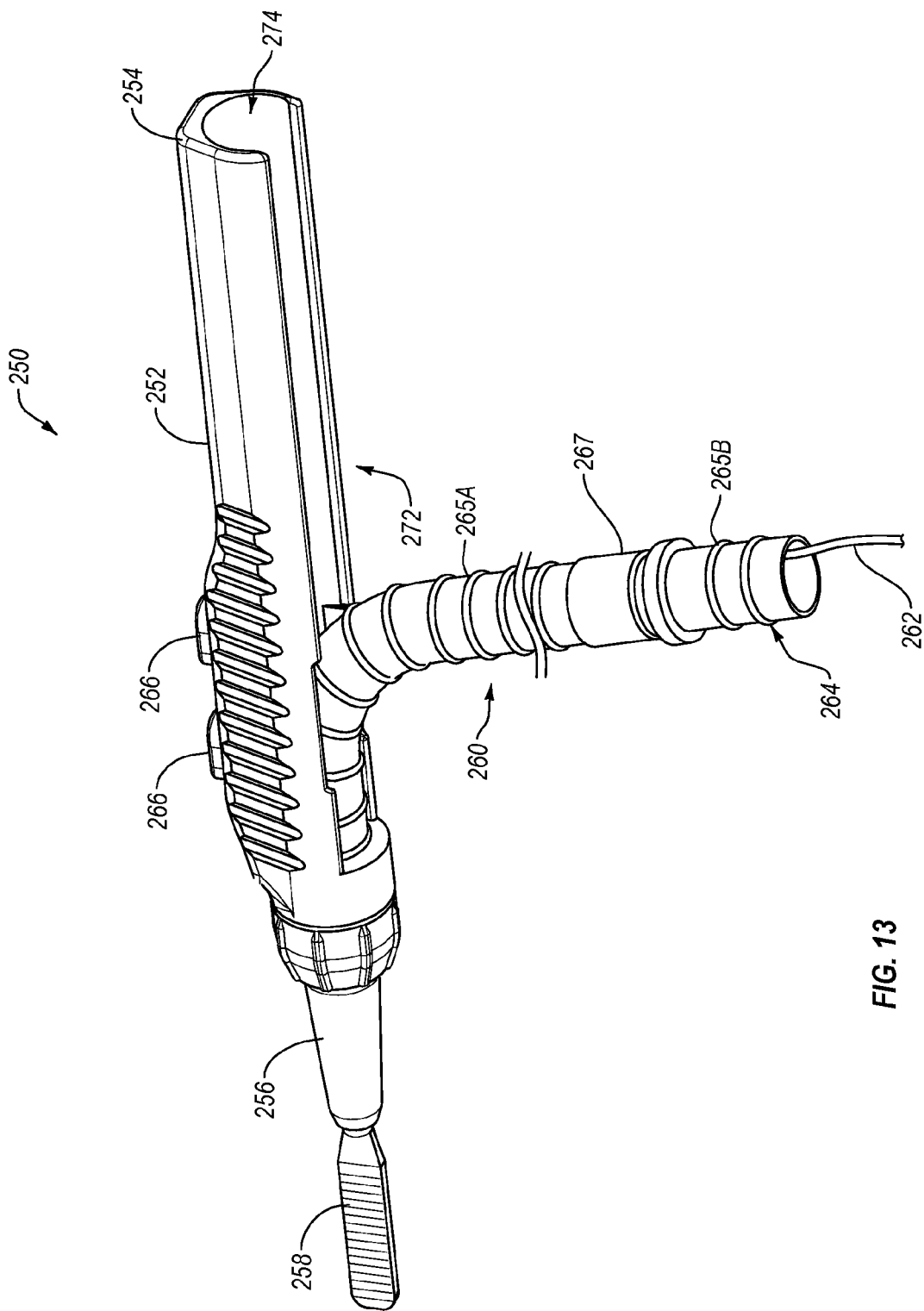
FIG. 13 is another bottom perspective view of the electrosurgical instrument of FIG. 10 showing another exemplary exit location for a utility conduit that is connected to the hand piece of the electrosurgical instrument.

Longitudinal channel 274 allows a physician to select the exit location of utility conduit 260 in much the same manner as described above with reference to longitudinal channels 168, 188, and 208. More particularly, a physician may select the exit location of utility conduit 260 by positioning differing lengths of utility conduit 260 within longitudinal channel 274. For instance, rather than filling the entire length of longitudinal channel 274 with utility conduit 260 as shown in FIG. 12, only a portion of longitudinal channel 274 may have utility conduit 260 positioned therein as shown in FIG. 13.

Channel system 272 is configured to allow a physician to select substantially any location along the length of longitudinal channel 274 as an exit location. For instance, a physician with a larger hand may desire utility conduit 260 to exit closer to proximal end 254. This can be accomplished by simply positioning more of utility conduit 260 within longitudinal channel 274 so that the exit location of utility conduit 260 is closer to proximal end 254. Alternatively, a physician with a smaller hand may desire utility conduit 260 to exit very near receptacle 268. This can be accomplished by positioning only a short length of utility conduit 260 within longitudinal channel 274. Thus, channel system 272 allows a physician to customize hand piece 252 so that hand piece 252 is most comfortable to that physician and reduces the resistance and fatigue caused by the weight of utility conduit 260.

Notably, by connecting utility conduit 260 adjacent distal end 256, hand piece 252 does not include or act as a smoke/fluid conveying conduit. That is, hand piece 252 does not have to include a channel or other conduit that extends from distal end 256 to proximal end 254 and that is sealed along its entire length. With a typical smoke evacuation device, a first seal is required between the nozzle and a distal end of a conduit in the hand piece and a second seal is required between a proximal end of the conduit in the hand piece and the smoke evacuation hose. Because utility conduit 260 is connected and sealed adjacent to intake 259, a second seal is not required between proximal end 254 and utility conduit 260.

Connecting utility conduit 260 near distal end 256 also provides a flow channel that has a generally uniform diameter from distal end 256 to an associated vacuum device. More specifically, the interior of utility conduit 260 provides a flow channel through which smoke/fluids may be conveyed away from a surgical site. Because utility conduit 260 has a generally uniform inner diameter throughout its length, the flow channel from distal end 256 of hand piece 252 to an associated vacuum device is generally uniform. As will be appreciated by one of ordinary skill in the art, a generally uniform flow channel provides increased flow efficiency of the smoke/fluid being conveyed away. In contrast, common smoke evacuation devices include a flow channel through a hand piece and a smoke evacuation hose that have different diameters, thereby reducing the flow efficiency therethrough.

In the illustrated embodiment, longitudinal channel 274 is shown having a generally straight and smooth interior surface. The generally straight and smooth interior surface of longitudinal channel 274 allows for utility conduit 260 to exit hand piece 252 at substantially any location along the length of longitudinal channel 274. Accordingly, longitudinal channel 274 allows for the exit location of utility conduit 260 to be continuously variable. In other words, the exit location of utility conduit 260 may be selectively adjusted to substantially any location along the length of longitudinal channel 274.

In other embodiments, however, longitudinal channel 274 may optionally be formed with one or more detents, similar to detents 190 shown in FIGS. 6-7, to facilitate secure holding of utility conduit 260 within longitudinal channel 274 and/or to create one or more predefined, discrete exit locations along the length of longitudinal channel 274. As with detents 190, the exit locations may be defined by the detents in longitudinal channel 274. Channel system 272 may also optionally include one or more side channels similar to side channels 170, 172, 184, 186, 204, and 206.

As can be seen in FIGS. 10, 12, and 13, at least a portion of utility conduit 260 may be corrugated, convoluted, fluted, or have detents disposed on the outer surface thereof. Like detents 212 described above, the corrugations, convolutions, flutes, or detents on utility conduit 260 may facilitate secure holding of utility conduit 260 within longitudinal channel 274 and/or to create one or more predefined, discrete exit locations along the length of longitudinal channel 274. As with detents 212, the exit locations may be defined by the corrugations, convolutions, flutes, or detents on utility conduit 260 rather than in longitudinal channel 274. It will be understood, however, that utility conduit 260 may not be corrugated, convoluted, fluted, or include detents thereon. Additionally, it is understood that any combination of a utility conduit (corrugated, convoluted, fluted, detented, or smooth) and channel (straight or detented) may be used.

Figure 14:
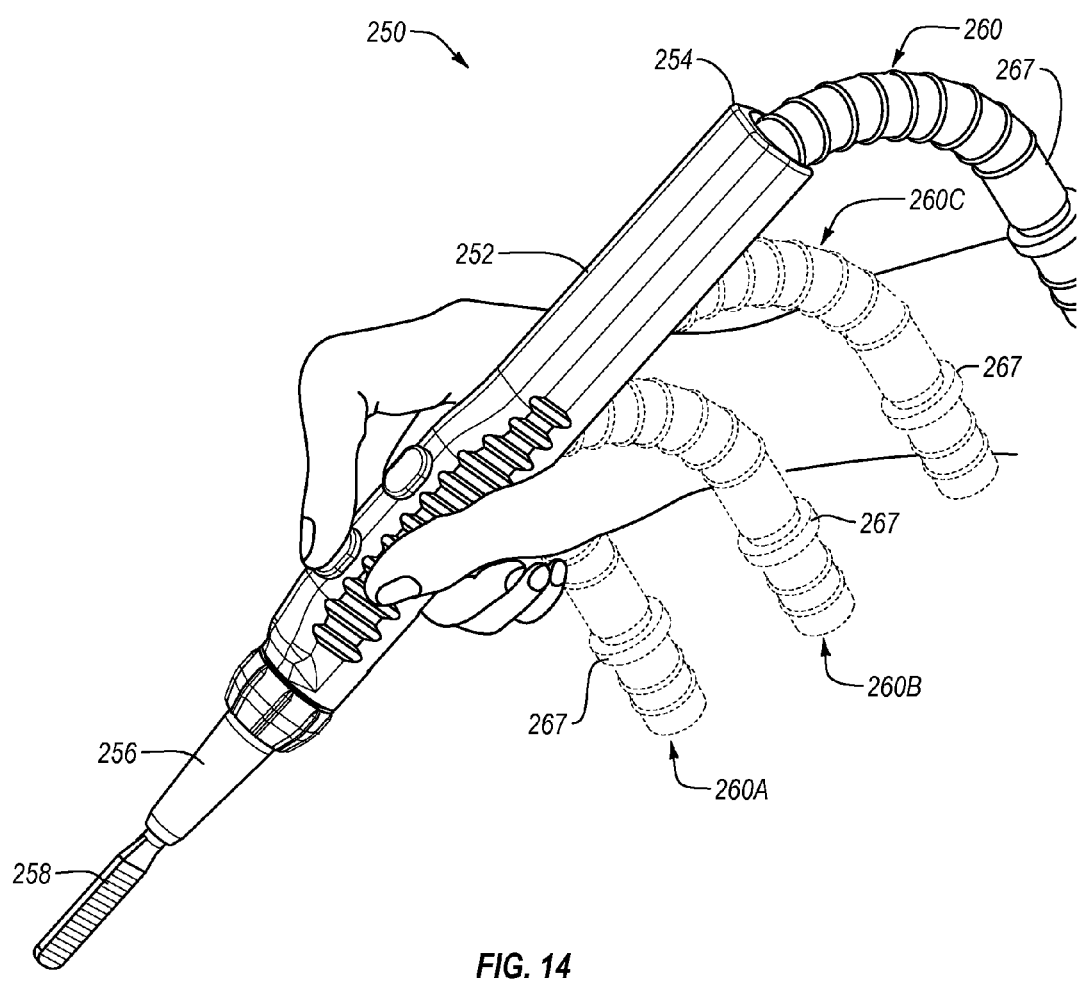
FIG. 14 illustrates the electrosurgical instrument of FIG. 10 being held with the utility conduit exiting the electrosurgical instrument from multiple exemplary exit locations.

FIG. 14 illustrates electrosurgical instrument 250 in use. Specifically, FIG. 14 illustrates a few examples of where and how utility conduit 260 may exit hand piece 252 and fall relative to a physician's hand. For instance, utility conduit 260A exits electrosurgical instrument 250 on the front side of the physician's palm so that utility conduit 260A is positioned in the palm of the physician's hand. As a result, the physician may grasp utility conduit 260A by wrapping some or all of his or her fingers around utility conduit 260A. While grasping utility conduit 260A, the physician may also hold hand piece 252 as shown in FIG. 14 (e.g., between the thumb and middle finger, with the index finger on top to control the input devices). In this arrangement, utility conduit 260A may act as a handle for electrosurgical instrument 250. Additionally, utility conduit 260A may be formed to provide stability to electrosurgical instrument 250. For instance, utility conduit 260A may be formed of or include a tubing that is stiff enough to maintain the position or orientation of hand piece 252 when utility conduit 260A is used as a handle. More specifically, utility conduit 260A may be stiff enough so that utility conduit 260A maintains hand piece 252 in its current position even when a physician lets go of hand piece 252 and is only holding utility conduit 260A. Furthermore, utility conduit 260A may be sized to comfortably fit within a physician's hand and allow for the physician to securely hold utility conduit 260A.

To provide the above noted stability and grip functionalities, a utility conduit may have an outer diameter of between about 0.1 inches and about 3 inches. In one example embodiment, a utility conduit has an outer diameter of about 0.5 inches. A utility conduit may also have some elastic flexibility that contributes to the above-noted functionality. For instance, a utility conduit may be formed to allow for the utility conduit to be angled or bent without collapsing or significantly reducing the inner lumen or flow channel therein. By way of example, the material used to form the utility conduit may allow the utility conduit to have a bend radius of between about 0° and about 180°. In the case of a utility conduit with a bend radius of about 180°, a swivel may be connected between the utility conduit and the hand piece to allow the utility conduit to extend away from the hand piece as shown in the Figures. In other embodiments, all or portions of a utility conduit may be segmented and joined together to provide a moving joint flexibility.

As noted, a utility conduit may be formed from multiple sections. The sections of the utility conduit may have diameters and/or flexibility characteristics that are different from one another. For instance, a first section connected to the hand piece may be relatively stiff to provide the above-noted stability and grip functionalities. In contrast, a second section connected to the first section may be more flexible than the first section.

As noted herein, a utility conduit may be formed by one or more cables and/or one or more hoses. Accordingly, the noted diameters and flexibilities may be a result of multiple hoses, cables, and/or combinations thereof. For instance, two or more hoses may have a combined diameter of between about 0.1 inches and about 3 inches.

The physician may further select an exit location near the crook of the physician's hand so that utility conduit 260B extends down the crook of the hand towards the wrist. The physician may further select an exit location for utility conduit 260C that is closer to proximal end 254. Still further, the physician may elect to have utility conduit 260 exit electrosurgical instrument 250 at proximal end 254, similar to a standard electrosurgical instrument.

As noted herein, a cable or hose that exits from a proximal end of a hand piece creates resistance, typically in the form of a torque, to the movement of the hand piece. Thus, when a user manipulates the hand piece, either to move the hand piece to a new location or to reorient the hand piece within the same general location, the cable or hose resists the movement or reorientation of the hand piece. Accordingly, allowing the exit location of utility conduit 260 to be adjusted along the length of hand piece 252 reduces the amount of resistance typically created by the cable or hose.

In addition to reducing the overall resistance typically created by a cable or hose, moving the exit location of utility conduit 260 closer to the distal end of hand piece 252 also reduces the change is resistance experienced when moving or reorienting hand piece 252. As a hand piece 252 is moved or reoriented, the resistance created by a cable or hose changes. While the change in resistance may be due at least in part to the direction of movement or reorientation and/or the speed of the movement, the change in resistance is primarily due to the exit location of the cable or hose. As discussed herein, the increased distance between the exit location and the pivot point of the hand piece creates a larger torque. As a result, when the exit location of the cable or hose is at or near the proximal end of the hand piece, the change in resistance during movement or reorientation of the hand piece is greater than the change in resistance created when the exit location is closer to the distal end of the hand piece.

With reference to FIG. 14, for instance, when utility conduit 260 extends out of proximal end 254 of hand piece 252, utility conduit 260 creates resistance to the movement of hand piece 252. Additionally, as hand piece 252 is moved or reoriented, the resistance created by utility conduit 260 changes. When utility conduit 260 exits hand piece 252 from a location closer to the distal end of hand piece 252, the resistance created by utility conduit 260 is reduced. Additionally, the change in resistance created by utility conduit 260 when hand piece 252 is moved or reoriented is also reduced as the exit location of utility conduit 260 moves toward the distal end of hand piece 252. When utility conduit 260 exits near the distal end of hand piece 252 (e.g., as illustrated by utility conduit 260A), the resistance and change in resistance created by utility conduit 260 falls dramatically. In such arrangements, the resistance and change in resistance may drop to near zero or at least negligible levels.

The following tables demonstrate that the amount of torque resulting from a distally located exit location is significantly lower than when the exit location is disposed at or near the proximal end of a hand piece. The torque resulting from the cables and/or hoses connected to numerous hand pieces were measured. Specifically, the torques associated with eleven different devices were measured at various heights and at various orientations. Devices 1-4 were standard electrosurgical instruments that include power cables extending from the proximal ends of the hand pieces. Devices 5-10 were electrosurgical instruments that include both power cables and smoke evacuation hoses extending from the proximal ends of the hand pieces. The torque associated with electrosurgical instrument 250 was also measured with utility conduit 260 extending from two different exit locations. The first exit location was at proximal end 254 as shown in FIG. 12. The second exit location was below user inputs 266 as shown in FIG. 13.

Table 1 includes the torques associated with the eleven devices when the hand pieces were in a level orientation (i.e., the proximal and distal ends of the hand pieces were at substantially the same height). In contrast, Table 2 includes the torques associated with the eleven devices when the hand pieces were held at a 45° angle with the distal end of the hand piece being disposed lower than the proximal end. In addition to measuring the torques when the devices were at different orientations, the torques were also measured when the hand pieces were held at different heights (i.e., 2.5 ft, 3 ft, 3.5 ft, and 4 ft).

Tables 1 and 2 also include other basic information regarding each of the evaluated devices. This information includes the lengths of the hand pieces, the masses of the hand piece and associated cables/hoses, and the distances between the pivot points of the hand pieces and the ends of the hand pieces. To provide consistency throughout the samples, the pivot point for each hand piece was determined to be at the user input button positioned closest to the proximal end of the hand piece.

As can be seen from the data in Tables 1 and 2, the power cables for the standard electrosurgical devices create torques ranging from 0.65 oz. in. to 3.5 oz. in. in the horizontal orientation and from 0.7 oz. in. to 3.5 oz. in. in the angled orientation. Similarly, the power cables and hoses for Devices

TABLE 1

| Electrosurgical Devices | Height above floor | | | | Center of Proximal Input Button to Tip (in.) | Center of Proximal Input Button to exit location (in.) | Total (in.) | Mass of hand piece, cord, & tubing (g) |
|---|---|---|---|---|---|---|---|---|
| | 2.5 ft | 3.0 ft | 3.5 ft | 4.0 ft | | | | |
| | Torque (oz. in.) | | | | | | | |
| Device 1 | 1.25 | 1.5 | 1.75 | 2 | 3.82 | 3.82 | 7.64 | 73.24 |
| Device 2 | 2 | 2.5 | 3 | 3.5 | 3.85 | 3.8 | 7.65 | 104.19 |
| Device 3 | 0.65 | 0.9 | 1.2 | 1.5 | 4.1 | 3.82 | 7.92 | 62.69 |
| Device 4 | 0.65 | 0.8 | 1 | 1.25 | 4.2 | 3.3 | 7.50 | 66.3 |
| Smoke Evac Devices | | | | | | | | |
| Electrosurgical Instrument 250 (utility conduit extending from proximal end) | 5 | 5.75 | 6.75 | 7 | 3.83 | 3.83 | 7.66 | 146.81 |
| Electrosurgical Instrument 250 (utility conduit exiting near input button) | 0 | 0 | 0 | 0 | 3.82 | 0.15 | 3.97 | 146.81 |
| Device 5 | 4.5 | 5.5 | 6.5 | 7 | 4.2 | 4 | 8.20 | 216.27 |
| Device 6 | 1.75 | 3 | 4.5 | 7.5 | 3.97 | 3.96 | 7.93 | 268.73 |
| Device 7 | 4.5 | 5.5 | 6.5 | 7.5 | 3.33 | 3.5 | 6.83 | 180.87 |
| Device 8 | 3.75 | 5.75 | 6 | 6.75 | 4.43 | 3.7 | 8.13 | 141.64 |
| Device 9 | 3.25 | 4.5 | 5.25 | 6.25 | 4.24 | 4.24 | 8.48 | 157.88 |
| Device 10 | 1.5 | 1.75 | 2 | 2.25 | 4.12 | 2.57 | 6.69 | 128.73 |

TABLE 2

| Electrosurgical Devices | Height above floor | | | | Center of Proximal Input Button to Tip (in.) | Center of Proximal Input Button to exit location (in.) | Total (in.) | Mass of hand piece, cord, & tubing (g) |
|---|---|---|---|---|---|---|---|---|
| | 2.5 ft | 3.0 ft | 3.5 ft | 4.0 ft | | | | |
| | Torque (oz. in.) | | | | | | | |
| Device 1 | 1.5 | 1.75 | 2 | 2.3 | 3.82 | 3.82 | 7.64 | 73.24 |
| Device 2 | 2.25 | 2.75 | 3.25 | 3.5 | 3.85 | 3.8 | 7.65 | 104.19 |
| Device 3 | 0.7 | 1.25 | 1.5 | 1.75 | 4.1 | 3.82 | 7.92 | 62.69 |
| Device 4 | 1 | 1.25 | 1.5 | 1.75 | 4.2 | 3.3 | 7.50 | 66.3 |
| Smoke Evac Devices | | | | | | | | |
| Electrosurgical Instrument 250 (utility conduit extending from proximal end) | 5 | 5.75 | 6.75 | 7 | 3.83 | 3.83 | 7.66 | 146.81 |
| Electrosurgical Instrument 250 (utility conduit exiting near input button) | 0 | 0 | 0 | 0 | 3.82 | 0.15 | 3.97 | 146.81 |
| Device 5 | 4.5 | 5.5 | 6.5 | 7 | 4.2 | 4 | 8.20 | 216.27 |
| Device 6 | 1.75 | 3 | 4.5 | 7.5 | 3.97 | 3.96 | 7.93 | 268.73 |
| Device 7 | 4.5 | 5.5 | 6.5 | 7.5 | 3.33 | 3.5 | 6.83 | 180.87 |
| Device 8 | 3.75 | 5.75 | 6 | 6.75 | 4.43 | 3.7 | 8.13 | 141.64 |
| Device 9 | 3.25 | 4.5 | 5.25 | 6.25 | 4.24 | 4.24 | 8.48 | 157.88 |
| Device 10 | 1.5 | 1.75 | 2 | 2.25 | 4.12 | 2.57 | 6.69 | 128.73 |

5-10 create torques ranging from 1.5 oz. in. to 7.5 oz. in. in both the horizontal and angled orientations. It is observed that the torque for each device generally increases as the height of the hand piece increases. This is understandable since the length, and thus the weight, of the suspended portion of the power cable and/or evacuation hose increases as the height of the hand piece increases.

With regard to electrosurgical instrument 250, it is noted that the torque from utility conduit 260 is significantly higher when utility conduit exits hand piece 252 at proximal end 254 than when utility conduit 260 exits hand piece 252 near user inputs 266. Specifically, when utility conduit exits hand piece 252 at proximal end 254, utility conduit 260 creates torques ranging from 5 oz. in. to 7 oz. in., depending on the height of hand piece 252. In contrast, when utility conduit 260 exits hand piece 252 near user inputs 266, utility conduit 260 creates no torque, or negligible levels of torque. In some embodiments, the utility conduit creates about 0 oz. in. of torque when the utility conduit exits the hand piece at the central portion or at about the midway point between the proximal and distal ends of the hand piece. Thus, by allowing the exit location of utility conduit 260 to be adjusted along the length of hand piece 252, a user can customize electrosurgical instrument 250 to provide torques ranging anywhere from about 0 oz. in. up to about 7 oz. in. or more.

It is understood that the features of the above described embodiments are not exclusive to one another. Rather, one of ordinary skill in the art will recognize that the described features can be combined and/or modified as may be needed or desired. For example, the channels of the various channel systems can have generally smooth interior surfaces or they can be formed with detents, either of which can receive a cable/hose/conduit with a generally smooth outer surface. Alternatively, the channels, whether with smooth surfaces or detents, can receive a cable/hose/conduit that has detents of its own formed thereon.

Furthermore, while some of the channel systems have been shown and described as having two opposing side channels and a single longitudinal channel, it will be understood that a channel system according to the present invention can be formed with a single side channel, a single longitudinal channel, multiple side channels, multiple longitudinal channels, or a combination thereof. For instance, a channel system may include one or more side channels along the length of the hand piece, each of which exits to the same side of the hand piece. A channel system may also have multiple side channels on each side of the hand piece. Furthermore, a channel system may have multiple channels, some sized for an electrical cable and some sized for an evacuation hose. Still further, a channel system may have one or more channels that are configured to receive and selectively retain an electrical cable and an evacuation hose in the same channel at the same time.

While the embodiments disclosed herein have been directed to electrosurgical instruments with adjustable utility conduits, the present invention is not intended to be limited only to electrosurgical instruments. Rather, the present invention is broadly directed to any hand-held instrument that has an adjustable utility conduit as described herein. More specifically, the present invention includes any hand-held instrument that has a channel system that allows for the selective adjustment of an exit location of a utility conduit from the hand-held instrument between proximal and distal ends of the hand-held instrument. Examples of such hand-held instruments may include, but are not limited to, dental instruments (e.g., drills, polishing tools, scalers, compressed air tools, suction tools, irrigation tools, carries detection tools, water flossing tool (e.g., waterpik)), soldering tools (e.g., heated tools, smoke collection tools, de-soldering tools), high speed grinding and polishing tools (e.g., Dremel tools, carving tools, manicure tools, dental lab grinders/polishers), laser treatment instruments, laser surgical instruments, light probes, suction handles (e.g., Yankauer), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy hand pieces, phaco hand pieces, shears, shaver, or razor hand pieces, micro drill hand pieces, vacuum hand pieces, small parts handling hand pieces, tattoo needle handles, small torch hand pieces, electrology hand pieces, low speed grinding, polishing and carving tools, permanent makeup hand pieces, electrical probe hand pieces, ferromagnetic surgical hand pieces, surgical suction instruments (e.g., liposuction cannulas), surgical suction cannulas, microdermabrasion hand pieces, fiberoptic camera handles, microcamera hand pieces, pH probe hand pieces, fiberoptic and LED light source hand pieces, hydrosurgery hand pieces, orthopedic shaver, cutter, burr hand pieces, wood burning tools, electric screwdrivers, electronic pad styluses, and the like.

Furthermore, the present invention is not limited to handheld instruments that allow for the adjustment of an exit location of a utility conduit therefrom. Rather, the present invention also encompasses hand-held instruments that have a utility conduit connected thereto and that extend therefrom at a location other than at the proximal end of the hand-held instrument. For instance, the exit location of the utility conduit may not be adjustable along the length of the hand-held instrument. Nevertheless, the exit location of the utility conduit may be positioned at a location along the length of the hand-held instrument that is away from the distal end of the hand-held instrument.

Even more specifically, the hand-held instrument may have a central portion disposed approximately midway between the proximal and distal ends of the instrument. The exit location of the utility conduit may be positioned at about the central portion of the hand-held instrument or between the central portion and the distal end of the hand-held instrument. The hand-held instrument may also have a three-quarter portion disposed approximately midway between the central portion and the proximal end. In other words, approximately one quarter of the length of the hand-held instrument is disposed between the proximal end and the three-quarter portion, while three quarters of the length of the hand-held instrument are disposed between the three-quarter portion and the distal end. The exit location of the utility conduit may be positioned at about the three-quarter portion of the hand-held instrument or between the three-quarter portion and the distal end of the hand-held instrument.

By way of example, the exit location may be positioned near a central portion of the hand-held instrument or between the central portion and the distal end of the hand-held instrument, similar to cables 160A and 160B in FIG. 5, cables 210A and 210B in FIG. 8, cable 222A in FIG. 9, utility conduit 260 in FIGS. 10 and 13, or utility conduit 260A in FIG. 14. The exit location may also be positioned between the central portion and the proximal end of the hand-held instrument, but away from the proximal end of the hand-held instrument. Positioning the exit location, whether fixed or adjustable, away from the proximal end of the hand-held instrument reduces the resistance from the utility conduit and thereby reduces the fatigue experienced by user of the hand-held instrument.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical instrument for use during an electrosurgical procedure to convey smoke/fluid away from a surgical site, the medical instrument comprising:
 a utility conduit comprising a smoke/fluid evacuation hose configured to convey smoke/fluid away from a surgical site; and
 a hand piece having a proximal end, a distal end having an intake, and a central portion disposed between the proximal and distal ends, the central portion having a receptacle to which the smoke/fluid evacuation hose is connected, the smoke/fluid evacuation hose being in fluid communication with the intake, the hand piece further comprising a channel system that enables at least a portion of the utility conduit to be selectively positioned within the channel system to thereby select an exit location from the channel system for the utility conduit, wherein the channel system enables the exit location to be selectively adjusted such that the exit location may be selectively moved along a length of the hand piece between the receptacle and the proximal end.

2. The electrosurgical instrument of claim 1, wherein the channel system comprises one or more discrete exit locations between the receptacle and the proximal end.

3. The electrosurgical instrument of claim 1, wherein the utility conduit comprises one or more electrical cables.

4. The electrosurgical instrument of claim 1, wherein the utility conduit comprises multiple smoke/fluid evacuation hoses.

5. The electrosurgical instrument of claim 1, wherein the utility conduit has an outer diameter of about 0.5 inches.

6. The electrosurgical instrument of claim 1, wherein the utility conduit comprises a first section and a second section, wherein the first section and second section are configured for relative rotational movement.

7. The electrosurgical instrument of claim 1, wherein the utility conduit creates a torque on the hand piece, and wherein the torque decreases from about 5.0 oz. in. when the utility conduit exits the hand piece adjacent the proximal end of the hand piece to about 0 oz. in. when the utility conduit exits the hand piece at the central portion.

8. A hand-held instrument comprising a hand piece and a utility conduit configured to transmit electrical energy from an electrical energy source to the hand piece and to convey smoke/fluid away from the hand piece, the hand piece comprising:
 a proximal end and a distal end, the distal end having a smoke/fluid intake therein;
 a receptacle disposed between the proximal end and the distal end and configured to have the utility conduit connected thereto;
 an input device configured to selectively control an operation of the hand-held instrument; and
 a channel system configured to selectively receive and retain therein at least a portion of the utility conduit, wherein the channel system enables an exit location of the utility conduit from the channel system to be selectively adjusted such that the exit location may be selectively moved along a length of the hand piece between the receptacle and the proximal end.

9. The hand-held instrument of claim 8, wherein the channel system comprises a longitudinal channel extending from the receptacle to the proximal end of the hand piece.

10. The hand-held instrument of claim 9, wherein the longitudinal channel comprises a plurality of detents spaced along a length of the longitudinal channel, the plurality of detents being configured to selectively retain at least a portion of the utility conduit within the longitudinal channel.

11. The hand-held instrument of claim 10, wherein the longitudinal channel further defines a plurality of predefined, discrete exit locations from which the utility conduit can exit the longitudinal channel.

12. The hand-held instrument of claim 11, wherein the plurality of predefined, discrete exit locations are formed along the length of the longitudinal channel and between the plurality of detents.

13. The hand-held instrument of claim 12, wherein the utility conduit defines an interior flow channel, the interior flow channel having a generally uniform diameter throughout the length of the utility conduit.

14. The hand-held instrument of claim 8, wherein the utility conduit creates a torque on the hand piece, and wherein the torque decreases from a maximum level when the utility conduit exits the hand piece adjacent to the proximal end to a minimum level when the utility conduit exits the hand piece at about the midway point between the proximal and distal ends of the hand piece.

15. The hand-held instrument of claim 14, wherein the maximum level of torque is between about 5 oz. in. and about 7 oz. in.

16. The hand-held instrument of claim 14, wherein the minimum level of torque is about 0 oz. in.

* * * * *

UNITED STATES PATENT AND TRADEMARK OFFICE
CERTIFICATE OF CORRECTION

Page 1 of 1

PATENT NO.         : 8,882,768 B2
APPLICATION NO.    : 13/831379
DATED              : November 11, 2014
INVENTOR(S)        : Greep et al.

It is certified that error appears in the above-identified patent and that said Letters Patent is hereby corrected as shown below:

In the specification

Column 13
Line 33-34, change "embodiment" to --embodiments--

Column 15
Line 43, change "that" to --than--

Column 18
Line 4, change "is" to --in--

Signed and Sealed this
Tenth Day of November, 2015

Michelle K. Lee
*Director of the United States Patent and Trademark Office*